(12) United States Patent
Sakuma et al.

(10) Patent No.: US 7,862,649 B2
(45) Date of Patent: Jan. 4, 2011

(54) PARTICULATE MATTER DETECTION DEVICE AND PARTICULATE MATTER DETECTION METHOD

(75) Inventors: Takeshi Sakuma, Nagoya (JP); Yasumasa Fujioka, Nagoya (JP); Atsuo Kondo, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 12/541,424

(22) Filed: Aug. 14, 2009

(65) Prior Publication Data

US 2010/0000404 A1 Jan. 7, 2010

Related U.S. Application Data

(63) Continuation of application No. PCT/JP2008/054825, filed on Mar. 14, 2008.

(30) Foreign Application Priority Data

Mar. 15, 2007 (JP) .............................. 2007-066626

(51) Int. Cl.
  *B03C 3/68* (2006.01)
(52) U.S. Cl. ..................... 96/19; 55/282.3; 55/DIG. 10; 95/3; 95/6; 95/7; 95/73; 95/74; 96/22; 96/23; 96/24; 96/28
(58) Field of Classification Search ............... 96/19–24, 96/28, 69; 95/3, 6, 7, 73, 74; 55/282.3, DIG. 10; 73/28.01, 28.02, 31.01–31.03
See application file for complete search history.

(56) References Cited

U.S. PATENT DOCUMENTS

| | | | | |
|---|---|---|---|---|
| 3,504,479 A | * | 4/1970 | Coe, Jr. ............................ 95/5 |
| 4,265,641 A | * | 5/1981 | Natarajan ....................... 95/79 |
| 5,515,262 A | * | 5/1996 | Johnston et al. ............... 363/90 |
| 5,542,964 A | * | 8/1996 | Kroeger et al. ................... 95/6 |
| 6,096,119 A | * | 8/2000 | Ho et al. ......................... 96/79 |
| 6,634,210 B1 | * | 10/2003 | Bosch et al. ................ 73/23.33 |
| 6,923,848 B2 | * | 8/2005 | Totoki ............................ 96/26 |
| 7,258,730 B2 | * | 8/2007 | Choi et al. ...................... 96/69 |
| 7,261,767 B2 | * | 8/2007 | Choi et al. ...................... 96/69 |
| 7,294,176 B2 | * | 11/2007 | Kim et al. ....................... 96/69 |

(Continued)

FOREIGN PATENT DOCUMENTS

JP 60-123761 7/1985

(Continued)

*Primary Examiner*—Richard L Chiesa
(74) *Attorney, Agent, or Firm*—Burr & Brown

(57) ABSTRACT

A particulate matter detection device includes a collection electrode that collects the particulate matter, a discharge electrode that allows a corona discharge to occur when a voltage is applied between the collection electrode and the discharge electrode, a measurement electrode, the impedance between the collection electrode and the measurement electrode changing when the collection electrode has collected the particulate matter, and a measurement section that detects a change in the impedance between the collection electrode and the measurement electrode, the particulate matter detection device detecting the particulate matter by charging the particulate matter contained in the gas by utilizing the corona discharge, collecting the charged particulate matter by the collection electrode by utilizing an electrostatic force, and detecting a change in the impedance between the collection electrode that has collected the particulate matter and the measurement electrode using the measurement section.

6 Claims, 6 Drawing Sheets

U.S. PATENT DOCUMENTS

| | | | |
|---|---|---|---|
| 7,507,275 B2 * | 3/2009 | Kim et al. ...................... 96/69 |
| 2003/0200787 A1 | 10/2003 | Totoki | |
| 2006/0107730 A1 | 5/2006 | Schumann | |
| 2008/0202331 A1 * | 8/2008 | Abdelkrim et al. ................ 95/5 |

FOREIGN PATENT DOCUMENTS

| | | | | |
|---|---|---|---|---|
| JP | 60-144945 | | 9/1985 | |
| JP | 61-142451 | | 6/1986 | |
| JP | 61-195462 | | 12/1986 | |
| JP | 63-286753 | | 11/1988 | |
| JP | 02-016445 | | 1/1990 | |
| JP | 2-72960 | | 6/1990 | |
| JP | 5-146717 | A * | 6/1993 | ................... 96/22 |
| JP | 6-39937 | | 5/1994 | |
| JP | 6-126210 | A * | 5/1994 | ................... 96/19 |
| JP | 2003-315244 | | 11/2003 | |
| JP | 2004-170287 | | 6/2004 | |
| JP | 2005-091043 | | 4/2005 | |
| JP | 2006-503270 | | 1/2006 | |
| JP | 2006-046281 | | 2/2006 | |

* cited by examiner

51a

51b

51c

PARTICULATE MATTER DETECTION DEVICE AND PARTICULATE MATTER DETECTION METHOD

FIELD OF THE INVENTION

The present invention relates to a particulate matter detection device and a particulate matter detection method. More particularly, the present invention relates to a particulate matter detection device and a particulate matter detection method that can simply detect particulate matter with a small measurement error.

BACKGROUND OF THE INVENTION

A flue gas or a diesel engine exhaust gas contains particulate matter (PM) (e.g., soot) that causes air pollution. A filter (diesel particulate filter (DPF)) formed of a ceramic or the like has been widely used to remove them. A DPF formed of a ceramic can be used for a long period of time, but may suffer defects (e.g., cracks) due to thermal deterioration or the like so that a small amount of particulate matter may leak from the DPF. It is very important to immediately detect such defects and abnormalities of apparatuses from the viewpoint of preventing air pollution. The amount of particulate matter discharged to the outside may increase when the amount of particulate matter contained in exhaust gas increases due to malfunction of a diesel engine or the like. In this case, it is important to detect the particulate matter contained in the exhaust gas to detect malfunction of a diesel engine or the like.

As a method of detecting particulate matter contained in exhaust gas, a particulate matter detection device may be provided on the downstream side of a DPF (see Patent Documents 1 to 5, for example).
Patent Document 1: JP-A-60-123761
Patent Document 2: JP-A-2006-503270
Patent Document 3: JP-B-6-39937
Patent Document 4: JP-A-2006-46281
Patent Document 5: JP-A-2005-91043

SUMMARY OF THE INVENTION

According to the invention disclosed in Patent Document 1, particulate matter is charged by causing a corona discharge, and an ion current due to the particulate matter is measured to determine the amount of the particulate matter. According to such a method where particulate matter is charged and ion current is detected, since the ion current due to the particulate matter is weak, a large-scale detection circuit is required to detect such a weak ion current so that costs increase. Moreover, since the particulate matter cannot be effectively charged when the exhaust gas flows at a high flow rate, the amount of particulate matter measured may be smaller than the amount of particulate matter actually contained in the exhaust gas (i.e., a large error may occur).

According to the invention disclosed in Patent Document 2, two electrodes are disposed in a soot/smoke passage. An ion current is caused to flow between the electrodes (space), and soot/smoke (particulate matter) that passes through the passage is charged by the ion current. The amount of particulate matter is determined by measuring a change in ion current when the particulate matter passes through the passage. According to this method, since the amount of charged particulate matter that passes through the passage is small, it is necessary to detect a change in ion current due to the particulate matter while causing an ion current at a picoampere (pA) level to flow between the electrodes. Therefore, a highly accurate current measurement circuit that takes noise into account is also required.

The present invention was conceived in view of the above problems. An object of the present invention is to provide a particulate matter detection device and a particulate matter detection method that can simply detect particulate matter with a small measurement error.

In order to achieve the above object, the present invention provides the following particulate matter detection devices and particulate matter detection methods.

According to a first aspect of the present invention, the particulate matter detection device that is disposed in a gas passage that allows gas containing particulate matter to pass through and detects the particulate matter contained in the gas, the particulate matter detection device comprising a collection electrode that collects the particulate matter, a discharge electrode that allows a corona discharge to occur when a voltage is applied between the collection electrode and the discharge electrode, a measurement electrode, providing an impedance between the collection electrode and the measurement electrode that changes when the collection electrode has collected the particulate matter, and a measurement section that detects a change in the impedance between the collection electrode and the measurement electrode, the particulate matter detection device detecting the particulate matter by charging the particulate matter contained in the gas by utilizing the corona discharge, collecting the charged particulate matter by the collection electrode by utilizing an electrostatic force, and detecting a change in the impedance between the collection electrode that has collected the particulate matter and the measurement electrode using the measurement section (first invention).

According to a second aspect of the present invention, the particulate matter detection device according to the first aspect is provided, further comprising a dielectric (inter-electrode dielectric) that is disposed on the side of the collection electrode opposite to the side that faces the discharge electrode, wherein the measurement electrode is disposed on the side of the inter-electrode dielectric opposite to the side on which the collection electrode is disposed.

According to a third aspect of the present invention, the particulate matter detection device according to the second aspect is provided, further comprising a dielectric (back-side dielectric) that is disposed on the side (back side) of the measurement electrode opposite to the side on which the inter-electrode dielectric is disposed, and a heater that is disposed on the surface of the back-side dielectric, wherein the particulate matter collected by the collection electrode is oxidized and removed by heat generated by the heater.

According to a fourth aspect of the present invention, the particulate matter detection device according to the second aspect is provided, further comprising a power supply that applies a voltage between the collection electrode and the measurement electrode so that a creeping discharge occurs on the surface of the inter-electrode dielectric, wherein the particulate matter collected by the collection electrode is oxidized and removed by the creeping discharge.

According to a fifth aspect of the present invention, the particulate matter detection device according to the first aspect is provided, further comprising a dielectric that is disposed on the side of the collection electrode opposite to the side that faces the discharge electrode, wherein the measurement electrode is disposed on the side of the dielectric on which the collection electrode is disposed.

According to a sixth aspect of the present invention, the particulate matter detection device according to the fifth aspect is provided, further comprising a heater that is disposed on the surface of the dielectric, wherein the particulate matter collected by the collection electrode is oxidized and removed by heat generated by the heater.

According to a seventh aspect of the present invention, the particulate matter detection method comprises a charging-collection step that charges particulate matter contained in gas by utilizing a corona discharge, and collects the charged particulate matter by a collection electrode by utilizing an electrostatic force, and a measurement step that detects a change in the impedance between the collection electrode that has collected the particulate matter and a measurement electrode to detect the particulate matter contained in the gas (second invention).

According to an eighth aspect of the present invention, the particulate matter detection method according to the seventh aspect is provided, wherein a change in the impedance between the collection electrode and the measurement electrode is detected after the charging-collection step in a state in which the corona discharge does not occur.

According to a ninth aspect of the present invention, the particulate matter detection method according to the seventh or eighth aspect is provided, wherein the charging-collection step and the measurement step are carried out using the particulate matter detection device according to any one of the first to the sixth aspects of the present invention.

According to a tenth aspect of the present invention, the particulate matter detection device that is disposed in a gas passage that allows gas containing particulate matter to pass through and detects the particulate matter contained in the gas, the particulate matter detection device comprising a dielectric, a collection electrode that is disposed on one side of the dielectric, a measurement electrode that is disposed on the other side of the dielectric, a discharge electrode that allows a corona discharge to occur when a voltage is applied between the collection electrode and the discharge electrode, and a measurement section that measures the voltage between the collection electrode and the measurement electrode, the particulate matter detection device detecting the particulate matter by charging the particulate matter contained in the gas by utilizing the corona discharge, and detecting the voltage between the collection electrode and the measurement electrode using the measurement section while collecting the charged particulate matter by the collection electrode that utilizes an electrostatic force (third invention).

According to an eleventh aspect of the present invention, the particulate matter detection device according to the tenth aspect is provided, further comprising a dielectric (back-side dielectric) that is disposed on the side (back side) of the measurement electrode opposite to the side on which the dielectric (inter-electrode dielectric) is disposed, and a heater that is disposed on the surface of the back-side dielectric, wherein the particulate matter collected by the collection electrode is oxidized and removed by heat generated by the heater.

According to a twelfth aspect of the present invention, the particulate matter detection device according to the tenth aspect is provided, further comprising a power supply that applies a voltage between the collection electrode and the measurement electrode so that a creeping discharge occurs on the surface of the inter-electrode dielectric, wherein the particulate matter collected by the collection electrode is oxidized and removed by the creeping discharge.

According to a thirteenth aspect of the present invention, the particulate matter detection method comprising charging particulate matter contained in gas by utilizing a corona discharge, and detecting the voltage between a collection electrode and a measurement electrode by a measurement section while collecting the charged particulate matter by the collection electrode by utilizing an electrostatic force to detect the particulate matter contained in the gas (fourth invention).

According to a fourteenth aspect of the present invention, the particulate matter detection method according to the thirteenth aspect is provided, wherein the particulate matter is detected using the particulate matter detection device according to any one of the tenth to twelfth aspects.

Since the particulate matter detection device according to the present invention (first invention) charges the particulate matter contained in the gas by utilizing a corona discharge, collects the charged particulate matter by the collection electrode, and detects a change in the impedance between the collection electrode and the measurement electrode to detect the particulate matter contained in the gas, the particulate matter can be detected by detecting a change in the impedance between the collection electrode and the measurement electrode due to the collected particulate matter. A change in impedance can be detected by detecting a change in current of about 10 nA (this value may vary depending on the measurement frequency and the measurement voltage). Therefore, the particulate matter can be simply detected while reducing any measurement errors.

Since the particulate matter detection method according to the present invention (second invention) includes the charging-collection step that charges the particulate matter contained in the gas by utilizing a corona discharge, and collects the charged particulate matter by the collection electrode by utilizing an electrostatic force, and the measurement step that detects a change in the impedance between the collection electrode that has collected the particulate matter and the measurement electrode to detect the particulate matter contained in the gas, the particulate matter can be simply detected while reducing the measurement error for the same reasons as for the particulate matter detection device according to the present invention.

Since the particulate matter detection device according to the present invention (third invention) charges the particulate matter contained in the gas by utilizing a corona discharge, and detects the voltage between the collection electrode and the measurement electrode while collecting the charged particulate matter by the collection electrode to detect the particulate matter contained in the gas, the particulate matter can be simply detected by detecting the voltage using a simple device. Moreover, since the detection device is rarely affected by the impedance of a cable or the like, the measurement error can be reduced. Furthermore, the particulate matter can be detected while collecting the particulate matter.

Since the particulate matter detection method according to the present invention (fourth invention) charges the particulate matter contained in the gas by utilizing a corona discharge, and detects the voltage between the collection electrode and the measurement electrode using the measurement section while collecting the charged particulate matter by the collection electrode by utilizing an electrostatic force to detect the particulate matter contained in the gas, the particulate matter can be simply detected while also reducing the measurement error for the same reasons as for the particulate matter detection device according to the present invention.

EXPLANATION OF SYMBOLS 1, 1*a*, 1*b*, 1*c*, 1*d*, 23*a*, 51, 51*a*, 51*b*, 51*c*: collection electrode, 2, 52: discharge electrode, 3, 24, 53: measurement section, 4, 54: inter-electrode dielectric, 5, 23*b*, 53: measurement electrode, 6, 56: back-side dielectric, 7, 57: heater, 8, 58: heat insulator, 9, 59: discharge power supply, 10, 60: corona discharge, 11, 61: charged particulate matter, 12, 62: arrow, 13, 63, 64: resistor, 14: switch, 15, 65: ground, 21, 21*a*, 21*b*, 21*c*: electrode extension section, 22: substrate, 31: diesel engine, 32: purification device, 33: charging-collection section, 34: sensor circuit, 36: calculation section, 37: exhaust pipe, 38: exhaust gas, 41: end, 42: support stage, 43: support member, 44: laminate, 45: fold, 46: rear end, 47: large-diameter portion, 48: small-diameter portion, 35, 100, 200: particulate matter detection device, a, b, c: distance

DETAILED DESCRIPTION OF THE INVENTION

Embodiments of the present invention are described in detail below with reference to the drawings. Note that the present invention is not limited to the following embodiments. Various modifications, improvements, and the like may be appropriately made with regard to the design without departing from the scope of the present invention based on common knowledge of a person skilled in the art.

(First invention)

(1) Particulate Matter Detection Device

Figure 1:
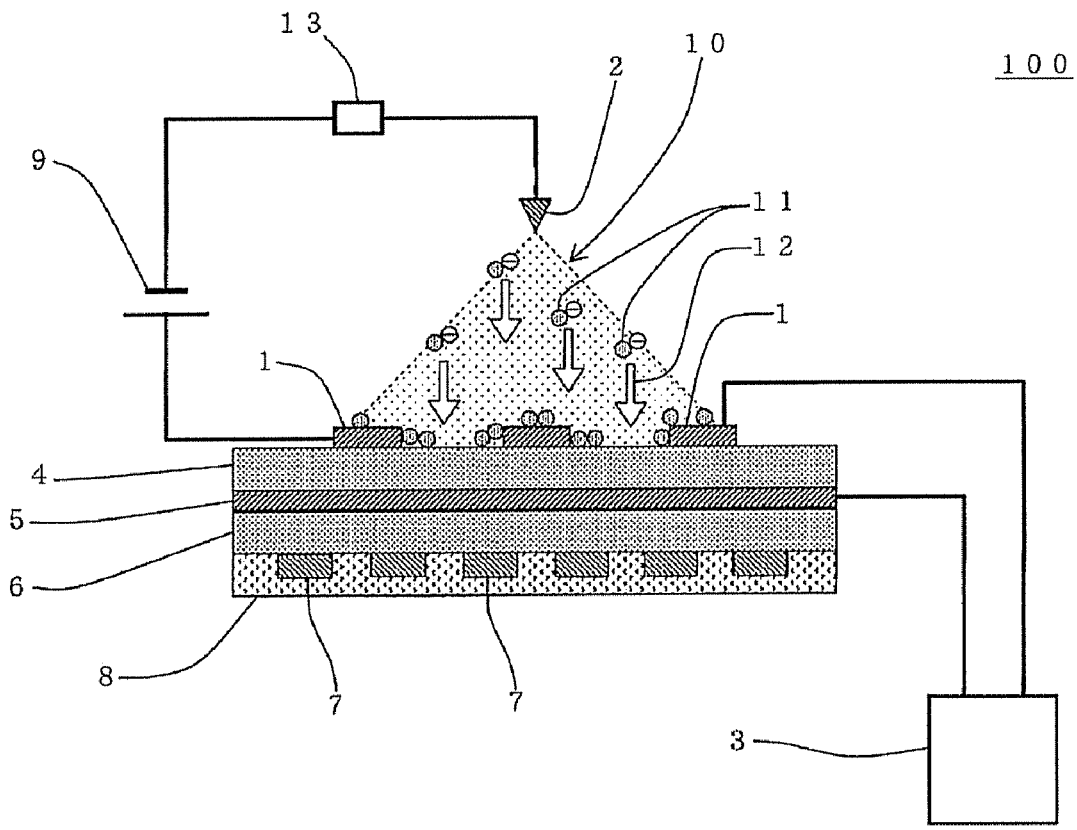
FIG. 1 is a cross-sectional view schematically showing a particulate matter detection device according to one embodiment of the present invention.

FIG. 1 is a cross-sectional view schematically showing a particulate matter detection device according to one embodiment of the present invention. As shown in FIG. 1, a particulate matter detection device 100 according to this embodiment includes a collection electrode 1 that collects particulate matter, a discharge electrode 2 that allows a corona discharge to occur when a voltage is applied between the collection electrode 1 and the discharge electrode 2, a measurement electrode 5, where the impedance between the collection electrode 1 and the measurement electrode 5 changes when the collection electrode 1 has collected the particulate matter, and a measurement section 3 that detects the change in the impedance between the collection electrode 1 and the measurement electrode 5. The particulate matter detection device 100 according to this embodiment is disposed in a gas passage that allows gas containing particulate matter to pass through and detects the particulate matter contained in the gas, while detecting the particulate matter by charging the particulate matter contained in the gas by utilizing a corona discharge, collecting the charged particulate matter by the collection electrode 1 by utilizing an electrostatic force, and detecting a change in the impedance between the collection electrode 1 that has collected the particulate matter and the measurement electrode 5 using the measurement section 3. The wording "detect a change in the impedance between the collection electrode and the measurement electrode" for the particulate matter detection device according to this embodiment may be used for directly measuring a resistance or a capacitance as the impedance, or measuring a change in the voltage between the collection electrode and the measurement electrode, or measuring a change in the amount of current that flows between the collection electrode and the measurement electrode, or measuring a change in the amount of charge stored between the collection electrode and the measurement electrode.

In the particulate matter detection device 100 according to this embodiment, a discharge power supply 9 is connected to the collection electrode 1 and the discharge electrode 2 to form a high-voltage circuit, as shown in FIG. 1. A high voltage is applied between the collection electrode 1 and the discharge electrode 2 from the discharge power supply 9 so that a corona discharge 10 occurs. Specifically, when a high voltage is applied between the collection electrode 1 and the discharge electrode 2, a corona discharge occurs between the discharge electrode 2 and the collection electrode 1 that serves as an opposite electrode (positive electrode). When the particulate matter passes through the area in which the corona discharge 10 occurs, the particulate matter is negatively charged due to the corona discharge. The charged particulate matter 11 is drawn toward the collection electrode 1 having an opposite polarity (positive electrode) due to an electrostatic force, and is collected by the collection electrode 1. An arrow 12 shown in FIG. 1 indicates a state in which the negatively charged particulate matter 11 is subjected to an electrostatic force in the direction indicated by the arrow 12. When the particulate matter is charged by utilizing a corona discharge and collected by utilizing an electrostatic force, the amount of particulate matter collected increases as the amount of particulate matter contained in the gas increases, and decreases as the amount of particulate matter contained in the gas decreases. A change in impedance to be detected varies depending on the amount of particulate matter collected. Therefore, the amount of particulate matter contained in the gas can be measured by detecting a change in impedance to detect the difference of the amount of particulate matter collected.

The distance between the collection electrode 1 and the discharge electrode 2 is preferably 5 to 50 mm, and more preferably 10 to 40 mm. If the distance between the collection electrode 1 and the discharge electrode 2 is within the above range, a corona discharge occurs more efficiently so that the particulate matter can be sufficiently collected. If the distance between the collection electrode 1 and the discharge electrode 2 is less than 5 mm, the measurement accuracy may decrease due to a decrease in collection rate. If the distance between the collection electrode 1 and the discharge electrode 2 is more than 50 mm, a higher voltage may be required (i.e., energy may be unnecessarily consumed). Note that the distance between the collection electrode 1 and the discharge electrode 2 refers to the radius of a virtual sphere that is drawn around the tip of the discharge electrode 2 and comes in contact with only part of the collection electrode 1.

It is preferable that the discharge power supply 9 is a power supply that can supply a stable direct-current voltage that allows a corona discharge to occur between the collection electrode 1 and the discharge electrode 2. For example, the discharge power supply 9 is preferably a power supply (discharge power supply) using a flyback power supply circuit or the like that stores energy from an input-side power supply in a transformer and discharges the stored energy to the output side to supply a high direct-current voltage. In the flyback power supply circuit, storage and discharge of energy into and from the transformer are controlled by a transistor or the like, and the output-side current is rectified by a diode. The voltage applied between the collection electrode 1 and the discharge electrode 2 is preferably 2 to 10 kV (DC), and more preferably 5 to 8 kV (DC). If the voltage is lower than 5 kV, a corona discharge may occur to only a small extent. If the voltage is higher than 10 kV, an arc discharge may occur, or a creeping discharge may occur on the surface of another member or the like. The current that flows between the collection electrode 1 and the discharge electrode 2 (corona discharge current) is preferably 1 mA or less, and more preferably 1 to 100 μA. If the current is less than 1 μA, the collection rate may decrease. It is desirable to reduce power consumption since it directly affects fuel consumption. The amount of power consumed by the power supply is preferably 10 W or less, and more preferably 1 W or less, taking account of a reduction in electromagnetic noise and the size of the circuit that causes a corona discharge. In the high-voltage circuit, the discharge power supply 9 is preferably connected to the discharge electrode 2 via a resistor 13. The resistor 13 is used as a limiting resistor that limits a current that flows between the discharge electrode 2 and the collection electrode 1 when the impedance between the discharge electrode 2 and the collection electrode 1 has decreased so that an arc discharge does not occur between the discharge electrode 2 and the collection electrode 1. Therefore, the resistor 13 preferably has a resistance of 500 kΩ to 20 MΩ, for example.

The discharge electrode 2 is preferably an electrode of which the end is formed at an acute angle. For example, the discharge electrode 2 preferably has a sharp end (e.g., in the shape of a needle, a rod, or a plate) so that electric field concentration occurs.

The collection electrode 1 serves as an opposite electrode for the discharge electrode 2 so that a corona discharge occurs, and also serves as a collection member (electrode) that collects the charged particulate matter.

Figure 2A:
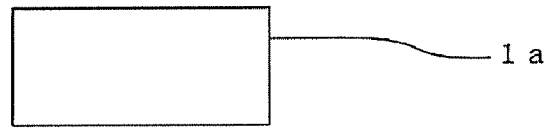
FIG. 2A is a plan view schematically showing the shape of a collection electrode.
Figure 2B:
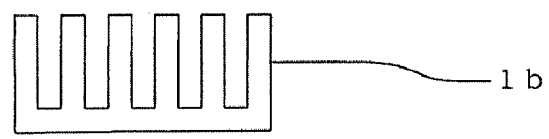
FIG. 2B is a plan view schematically showing the shape of a collection electrode.
Figure 2C:
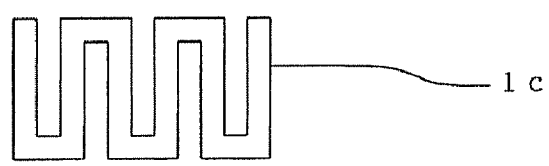
FIG. 2C is a plan view schematically showing the shape of a collection electrode.

The collection electrode may be a plate-shaped electrode (collection electrode 1a) that has a rectangular external profile, as shown in FIG. 2A. Note that it is preferable that the collection electrode is a plate-shaped electrode that has an external profile provided with elevations or depressions, as shown in FIGS. 2B and 2C. Note that the expression "provided with elevations or depressions" used herein refers to a case where the external profile is provided with both elevations and depressions, a case where the external profile is provided with only depressions, and a case where the external profile is provided with only elevations. FIGS. 2A, 2B, and 2C are plan views schematically showing the collection electrode. The collection electrode 1 shown in FIG. 2B differs from the rectangular collection electrode shown in FIG. 2A in that one side of the collection electrode 1 is provided with a plurality of depressions and elevations. In other words, a plurality of elevations are formed in FIG. 2B in a comb-like configuration. Specifically, the terms "depression" and "elevation" may be interchangeably used. Such a case is also included within the scope of the expression "provided with elevations or depressions". The collection electrode 14 shown in FIG. 2C differs from the rectangular collection electrode shown in FIG. 2A in that two parallel sides of the collection electrode are alternately provided with a plurality of depressions. Note that the collection electrode may have a shape in which the external profile is rectangular and is not provided with depressions and elevations and one or more slits (which is formed in a state where outer edge is remained) are formed in the collection electrode inside the outer edge. The external profile is not limited to a rectangle, but may be a polygon (e.g., pentagon), a circle, an oval, a track, or the like. Alternatively, the collection electrode may have a shape in which the external profile is provided with depressions and elevations and one or more slits are formed inside the outer edge. The collection electrode 1 of the particulate matter detection device 100 shown in FIG. 1 has a comb-like configuration (see FIG. 2B). FIG. 1 shows the cross section of the collection electrode 1 perpendicular to the direction in which the plurality of elevations extend.

The thickness of the collection electrode 1 is not particularly limited insofar as the collection electrode 1 exhibits sufficient durability and does not hinder the flow of exhaust gas. The area of the collection electrode 1 is not particularly limited insofar as the impedance sufficiently changes when the collection electrode 1 has collected the particulate matter, and electric power is not unnecessarily consumed when cleaning the adhering particulate matter. The size of the collection electrode 1 is not particularly limited, but is preferably 900 mm$^2$ or less. The number of collection electrodes 1 is not particularly limited. An arbitrary number of collection electrodes 1 may be provided.

Figure 3:
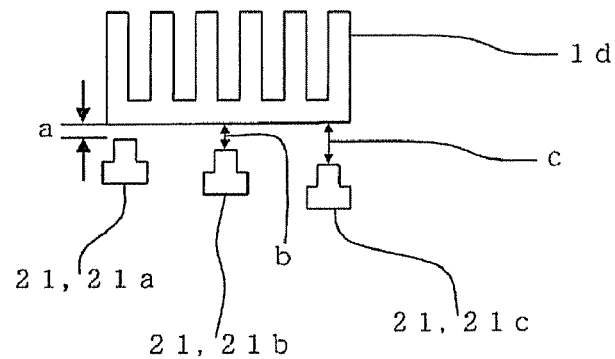
FIG. 3 is a plan view schematically showing a collection electrode and an electrode extension section.

In the particulate matter detection device 100 according to this embodiment in addition to the collection electrode 1, it is preferable to dispose at least one electrode extension section at a position where not to come in contact with the collection electrode 1. As shown in FIG. 3, it is more preferable to dispose a plurality of electrode extension sections 21 at a position that does not come into contact with a collection electrode 1d, for example. It is preferable that the collection electrode 1d and the electrode extension section 21 be electrically connected when the particulate matter collected by the collection electrode 1d has accumulated between the collection electrode 1d and the electrode extension section 21. The impedance of the collection electrode 1d gradually changes while the particulate matter is collected by the collection electrode 1d (i.e., when the collection electrode 1d and the electrode extension section 21 are not electrically connected), and rapidly increases when the collection electrode 1d and the electrode extension section 21 have been electrically connected so that it is possible to determine that a given amount of particulate matter has been collected. When a plurality of electrode extension sections 21 are disposed (see FIG. 3), it is preferable that the electrode extension sections 21 (21a, 21b, 21c) differ in the distance (a, b, c) from the collection electrode 1d. The amount of particulate matter collected by the collection electrode 1*d* can be determined stepwise when the electrode extension sections 21 (21*a*, 21*b*, 21*c*) differ in the distance (a, b, c) from the collection electrode 1*d*. In this case, the distances between the electrode extension sections 21 (21*a*, 21*b*, 21*c*) are not particularly limited, but it is preferable that the distances between the electrode extension sections 21 (21*a*, 21*b*, 21*c*) are longer than the distance (a, b, c) between the collection electrode 1*d* and each electrode extension section 21 (21*a*, 21*b*, 21*c*).

It is preferable that the material for each of the collection electrode 1, the discharge electrode 2, and the electrode extension section 21 contain at least one component selected from the group consisting of gold, silver, platinum, nickel, molybdenum, stainless steel, and tungsten. The content of these components is preferably 20 vol % or more, and more preferably 60 vol % or more.

As shown in FIG. 1, it is preferable that the particulate matter detection device 100 according to this embodiment further include a dielectric (inter-electrode dielectric) 4 that is disposed on the side of the collection electrode 1 opposite to the side that faces the discharge electrode 2, and the measurement electrode 5 is disposed on the surface of the inter-electrode dielectric 4 (i.e., the side opposite to the side on which the collection electrode 1 is disposed). It is preferable that the measurement section 3 is connected to the collection electrode 1 and the measurement electrode 5 to form a measurement circuit, and the measurement circuit detect a change in the impedance between the collection electrode 1 and the measurement electrode 5 using the measurement section 3 to detect the particulate matter. The particulate matter detection device 100 according to this embodiment measures a change in the impedance between the collection electrode 1 and the measurement electrode 5 as an alternating-current impedance. The alternating-current impedance is a synthetic impedance of a resistance component and a capacitance component between the collection electrode 1 and the measurement electrode that change due to adhesion of the particulate matter. Note that only the component that significantly affects a change in impedance may be measured. It is preferable that the particulate matter detection device 100 according to this embodiment detect the capacitance component since the capacitance between the collection electrode 1 and the measurement electrode 5 changes to a large extent. Note that a change in impedance may also be detected by measuring a change in current using a constant voltage source or measuring a change in voltage using a constant current source. When the capacitance changes to a large extent, a change in the amount of charge (amount of charge Q=applied voltage V×capacitance) that flows between the collection electrode 1 and the measurement electrode 5 may be measured. As the measurement voltage, an alternating-current voltage (e.g., rectangular wave or triangular wave) may be used instead of a sine wave. The particulate matter can be detected with high sensitivity without being affected by the outside environment by measuring a change in the capacitance (F) between the collection electrode 1 and the measurement electrode 5 as a change in the impedance between the collection electrode 1 and the measurement electrode 5. Moreover, the particulate matter detection device 100 can be reduced in size and produced inexpensively.

The distance between the collection electrode 1 and the measurement electrode 5 is not particularly limited insofar as a change in capacitance (impedance) due to the particulate matter collected by the collection electrode 1 can be accurately detected. The distance between the collection electrode 1 and the measurement electrode 5 is preferably 10 to 1000 μm, and more preferably 25 to 250 μm, for example. If the distance between the collection electrode 1 and the measurement electrode 5 is within the above range, the capacitance (impedance) between the collection electrode 1 and the measurement electrode 5 can be set so that a change in capacitance due to the particulate matter collected by the collection electrode 1 can be accurately detected. Since the distance between the collection electrode 1 and the measurement electrode 5 is equal to the thickness of the inter-electrode dielectric 4, it is preferable to set the thickness of the inter-electrode dielectric 4 within the above range.

The capacitance between the collection electrode 1 and the measurement electrode 5 when the particulate matter is not collected is preferably 5 to 100 pF (picofarad), and more preferably 10 to 50 pF. If the capacitance between the collection electrode 1 and the measurement electrode 5 is less than 5 pF, the capacitance of an external circuit may affect the measurement. If the capacitance between the collection electrode 1 and the measurement electrode 5 is more than 100 pF, measurement power may be required.

The measurement electrode 5 is not particularly limited insofar as a charge stored between the collection electrode 1 and the measurement electrode 5 and a change in capacitance (impedance) due to the particulate matter collected by the collection electrode 1 can be accurately detected. It is preferable that the measurement electrode 5 have a size almost equal to the size (area) of the external profile of the collection electrode 1 (on the assumption that elevations and depressions are not formed), for example. It is preferable that the measurement electrode 5 is disposed at such a position that the entire collection electrode 1 overlaps the measurement electrode 5 when moving the collection electrode 1 in the direction normal to the collection electrode 1. The thickness of the measurement electrode 5 is not particularly limited, but is preferably 5 to 100 μm, and more preferably 10 to 50 μm, for example. It is preferable that the material for the measurement electrode 5 contain at least one component selected from the group consisting of gold, silver, platinum, nickel, molybdenum, stainless steel, and tungsten. The content of these components is preferably 20 vol % or more, and more preferably 60 vol % or more.

The material for the inter-electrode dielectric 4 is not particularly limited, but is preferably a ceramic. It is more preferable that the material for the inter-electrode dielectric 4 contain at least one component selected from the group consisting of alumina, magnesium oxide, silicon oxide, silicon nitride, aluminum nitride, zirconia, cordierite, mullite, spinel, a magnesium-calcium-titanium oxide, a barium-titanium-zinc oxide, and a barium-titanium oxide. A dielectric containing such a compound rarely breaks even if a change in temperature occurs (i.e., exhibits excellent thermal impact resistance).

It is preferable that the measurement section 3 include a power supply that applies a measurement voltage between the collection electrode 1 and the measurement electrode 5, and a measuring device. The voltage applied from the power supply is not particularly limited, but is preferably 1 to 60 V, and more preferably 2 to 30 V. If the voltage applied from the power supply is less than 1 V, a detection signal may be reduced so that the measurement may be affected by noise. If the voltage applied from the power supply is more than 60 V, it may be impossible to use a general-purpose IC. The power supply must be an alternating-current power supply since the particulate matter detection device 100 according to this embodiment utilizes an insulating material (dielectric) between the collection electrode 1 and the measurement electrode 5. The measurement frequency is not particularly limited, but is preferably 300 kHz or less. The measuring device is not particularly limited. For example, an LCR meter that can measure an alternating-current impedance, a capacitance, or the like may be used.

When measuring the alternating-current impedance, the capacitance, or the like between the collection electrode 1 and the measurement electrode 5 using the measurement section 3, it is preferable to stop applying a high voltage between the collection electrode 1 and the discharge electrode 2 so that a corona discharge does not occur. If the alternating-current impedance or the like between the collection electrode 1 and the measurement electrode 5 is measured in a state in which a high voltage is applied between the collection electrode 1 and the discharge electrode 2, an accurate measured value of the alternating-current impedance or the like cannot be steadily obtained since the collected particulate matter is charged.

Figure 4:
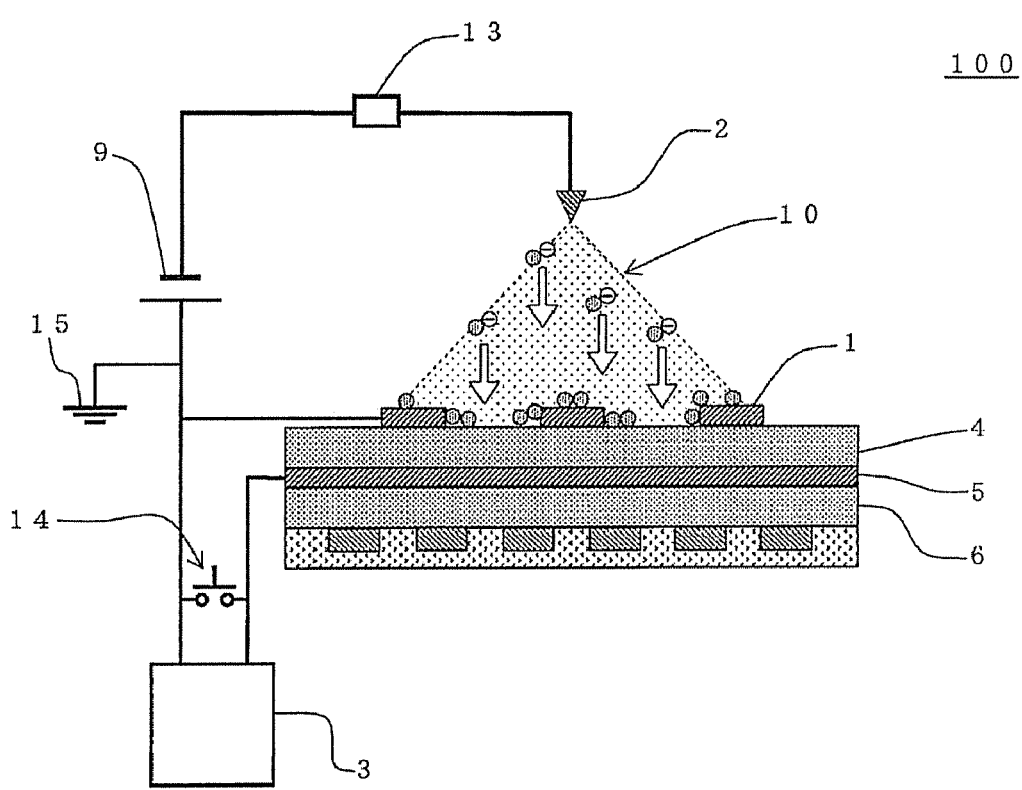
FIG. 4 is a cross-sectional view schematically showing a particulate matter detection device according to one embodiment of the present invention.

As shown in FIG. 4, it is preferable to provide a switch 14 that short-circuits the collection electrode 1 and the measurement electrode 5 in the measurement circuit, and short-circuit the collection electrode 1 and the measurement electrode 5 or connect the collection electrode 1 and the measurement electrode 5 through a resistor having a low resistance when causing a corona discharge to occur between the discharge electrode 2 and the collection electrode 1. This prevents a situation in which the measurement electrode 5 is charged during a corona discharge. If the measurement electrode 5 is charged during a corona discharge, a high-voltage current may be discharged from the charged measurement electrode 5 to the measurement section 3 when measuring the alternating-current impedance or the like so that an excessive load may be applied to the measurement section. In this case, since a charge flows into the measuring device, the alternating-current impedance or the like may not be accurately measured. The situation in which an excessive load is applied to the measurement section can be prevented by either short-circuiting the collection electrode 1 and the measurement electrode 5 together, or by connecting the collection electrode 1 and the measurement electrode 5 through a resistor having a low resistance which further prevents the measurement electrode 5 from being charged, thereby protecting the measurement section. As shown in FIG. 4, it is preferable to connect a line that is connected to the collection electrode 1 to a ground 15 so that the dielectric can be prevented from being charged when short-circuiting the collection electrode 1 and the measurement electrode 5, or connecting the collection electrode 1 and the measurement electrode 5 through a resistor having a low resistance. FIG. 4 is a cross-sectional view schematically showing the particulate matter detection device according to one embodiment of the present invention.

Figure 5:
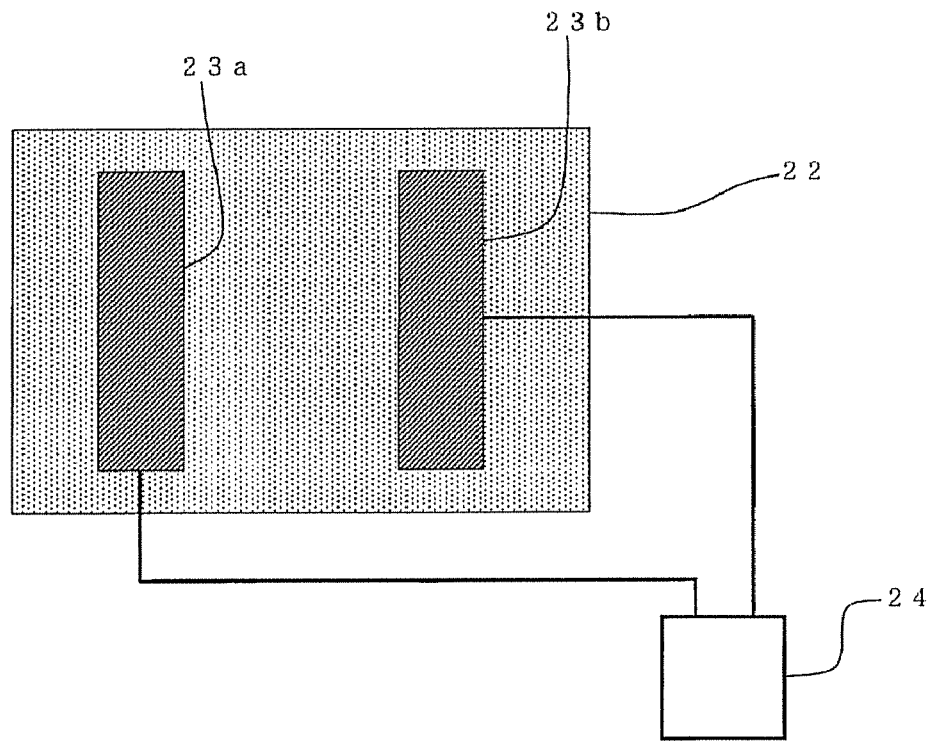
FIG. 5 is a plan view schematically showing a collection electrode and a measurement electrode used in a particulate matter detection device according to another embodiment of the present invention.

The particulate matter detection device according to the present invention may further include a dielectric that is disposed on the side of the collection electrode opposite to the side that faces the discharge electrode, and the measurement electrode may be disposed on the side of the dielectric on which the collection electrode is disposed. As shown in FIG. 5, a collection electrode 23a and a measurement electrode 23b may be separately disposed on a substrate formed of a dielectric 22, and a measurement section 24 may be connected between the collection electrode 23a and the measurement electrode 23b to detect a change in the impedance between the collection electrode 23a and the measurement electrode 23b, for example. Note that the expression "the collection electrode 23a and the measurement electrode 23b are separately disposed" means that the collection electrode 23a and the measurement electrode 23b are not spatially connected. FIG. 5 is a plan view schematically showing the collection electrode, the measurement electrode, and the measurement section used in the particulate matter detection device according to another embodiment of the present invention. When the collection electrode 23a and the measurement electrode 23b are disposed accordingly, the impedance of the collection electrode 23a changes as the particulate matter is collected by the collection electrode 23a. Therefore, the amount of particulate matter collected can be measured by detecting a change in impedance using the measurement section 24 so that the amount of particulate matter contained in the exhaust gas can be determined. A voltage may also be applied between the measurement electrode 23b and the discharge electrode when the collection electrode 23a collects the particulate matter so that the measurement electrode 23b also collects the particulate matter. In this case, since the area of the collection electrode increases, the particulate matter can be collected more efficiently. The distance between the collection electrode 23a and the measurement electrode 23b is preferably 5 to 10,000 μm. The length and the width of each of the collection electrode 23a and the measurement electrode 23b are not particularly limited, but are preferably 100 to 30,000 μm and 100 to 10,000 μm, respectively. The particulate matter detection device according to this embodiment is preferably configured in the same manner as the particulate matter detection device according to one embodiment of the present invention shown in FIG. 1, except that the collection electrode 23a and the measurement electrode 23b are disposed on the same side of the dielectric 22. In the example shown in FIG. 5, since conductive soot adheres between the collection electrode 23a and the measurement electrode 23b, the measurement voltage of the measurement section 24 may be an alternating-current voltage or a direct-current voltage.

As shown in FIG. 1, it is preferable that the particulate matter detection device 100 according to this embodiment further includes a dielectric (back-side dielectric) 6 that is disposed on the side (back side) of the measurement electrode 5 opposite to the side on which the inter-electrode dielectric 4 is disposed, and a heater 7 disposed on the surface of the back-side dielectric 6 (i.e., the side opposite to the side on which the measurement electrode 5 is disposed). It is preferable that a heater power supply (not shown) be connected to the heater 7, and the particulate matter collected by the collection electrode 1 is oxidized and removed by heat generated by the heater 7. The particulate matter detection device according to this embodiment can repeatedly and accurately detect the particulate matter by oxidizing and removing the particulate matter collected by the collection electrode 1 (i.e., cleaning the collection electrode 1). In the particulate matter detection device according to another embodiment of the present invention shown in FIG. 5, it is preferable to dispose a heater on the side of the dielectric opposite to the side on which the collection electrode is disposed, and oxidize and remove the particulate matter.

The material for the heater 7 is preferably platinum, tungsten, molybdenum, tungsten carbide, or the like. Among these, it is preferable to use platinum that exhibits an accurate resistance-temperature relationship. Since the temperature of the heater 7 can be accurately calculated from the resistance of the material by utilizing platinum as the material for the heater 7, the temperature of the heater 7 can be controlled with high accuracy. The shape and the size of the heater 7 are not particularly limited insofar as the particulate matter collected by the collection electrode 1 can be burned. As the heater power supply (not shown), it is preferable to use a step-down chopper power supply. This makes it possible to efficiently control the temperature of the heater 7. In this case, the switching frequency is preferably 20 kHz or more, and more preferably 20 to 100 kHz. A current applied to the heater 7 from the heater power supply is preferably 0.8 to 4 A. The amount of power consumed by the heater power supply is preferably 30 W or less.

The temperature when oxidizing and removing the particulate matter using the heater 7 is preferably 500 to 900° C., and more preferably 550 to 700° C. If the temperature is less than 500° C., the particulate matter may not be oxidized and removed. If the temperature is more than 900° C., the life of the element may decrease. The period of time in which the particulate matter is oxidized and removed using the heater 7 is preferably 1 to 120 seconds, and more preferably 3 to 30 seconds. If the period of time is less than 1 second, the particulate matter may not be sufficiently oxidized and removed. If the period of time is more than 120 seconds, unnecessary energy consumption may occur. It is preferable to appropriately heat the heater 7 during detection of a change in impedance or during a corona discharge so as to prevent effects of water (e.g., condensation) when detecting a change in the impedance between the collection electrode and the measurement electrode so that water does not adhere to the collection electrode, for example. In this case, the heating temperature is preferably 200 to 300° C.

As shown in FIG. 1, the particulate matter detection device 100 according to this embodiment preferably includes a sheet-shaped heat insulator 8 that is disposed to cover the heater 7. This suppresses radiation of heat generated by the heater 7 so that heat generated by the heater 7 can be efficiently utilized to burn the particulate matter. The material for the heat insulator 8 is not particularly limited, but is preferably a ceramic. It is more preferable that the material for the heat insulator 8 contain at least one component selected from the group consisting of alumina, magnesium oxide, silicon oxide, silicon nitride, aluminum nitride, zirconia, cordierite, mullite, spinel, a magnesium-calcium-titanium oxide, a barium-titanium-zinc oxide, and a barium-titanium oxide. As the ceramic, a porous ceramic, a ceramic fiber, or the like is preferably used. The thickness of the heat insulator 8 is not particularly limited insofar as radiation of heat can be suppressed. The thickness of the heat insulator 8 is preferably about 100 to 1000 μm, for example.

A particulate matter detection device according to another embodiment of the present invention may not include the heater 7, the heater power supply (not shown), and the heat insulator 8 that are included in the particulate matter detection device according to one embodiment of the present invention shown in FIG. 1, but may include a power supply (creeping discharge power supply (not shown)) that applies a voltage between the collection electrode 1 and the measurement electrode 5 so that a creeping discharge occurs on the surface of the inter-electrode dielectric 4. The particulate matter collected by the collection electrode can be oxidized and removed by providing the creeping discharge power supply and causing a creeping discharge to occur on the surface of the inter-electrode dielectric. It is preferable to use an alternating-current power supply, a pulse power supply, or the like as the creeping discharge power supply. A voltage applied when causing a creeping discharge is preferably 2 to 15 kV although the voltage differs depending on the thickness of the dielectric and the electrode structure. The amount of power required for causing a creeping discharge is preferably 10 to 30 W. The period of time in which the particulate matter is oxidized and removed by causing a creeping discharge is preferably 1 to 120 seconds, and more preferably 3 to 30 seconds. If the period of time is less than 1 second, the particulate matter may not be sufficiently oxidized and removed. If the period of time is more than 120 seconds, unnecessary energy consumption may occur. The particulate matter detection device according to this embodiment is preferably configured in the same manner as the particulate matter detection device according to one embodiment of the present invention shown in FIG. 1, except that the particulate matter detection device according to this embodiment does not include the heater 7, the heater power supply (not shown), and the heat insulator 8, but includes the creeping discharge power supply. Note that the particulate matter detection device according to another embodiment of the present invention shown in FIG. 5 may be configured so that the particulate matter is oxidized and removed by causing a creeping discharge.

Figure 6:
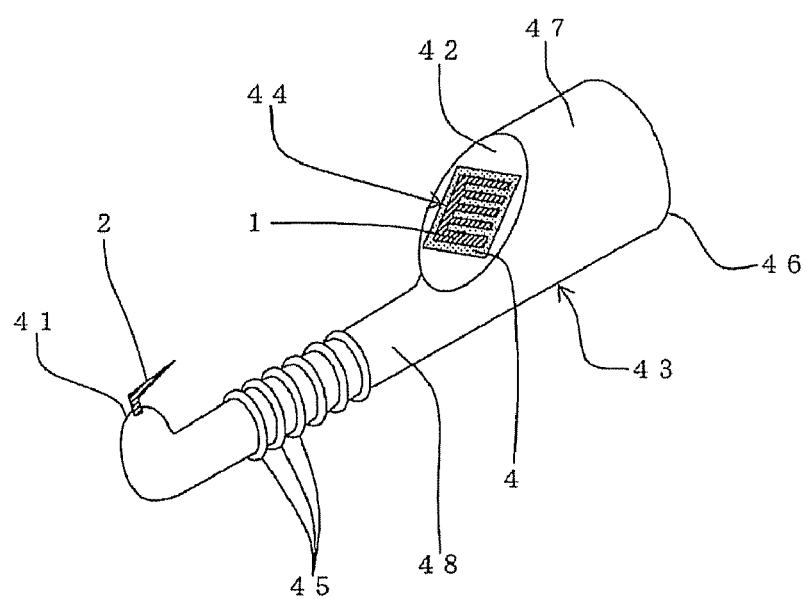
FIG. 6 is a perspective view schematically showing a state in which a laminate (e.g., collection electrode) and a discharge electrode are disposed on a support member.

It is preferable that the particulate matter detection device according to one embodiment of the present invention further include a support member, and a laminate 44 (see FIG. 6) that includes the collection electrode 1, the inter-electrode dielectric 4, the measurement electrode 5, the back-side dielectric 6, the heater 7, and the heat insulator 8. The laminate 44 and the discharge electrode 2 are preferably secured on the support member. As shown in FIG. 6, it is preferable that the laminate 44 and the discharge electrode 2 are disposed on a rod-shaped support member 43 that has an end 41 and a support stage 42, for example. It is preferable that the laminate 44 is embedded in the support stage 42 so that the collection electrode 1 and the inter-electrode dielectric 4 are exposed, and the discharge electrode 2 is disposed on the end 41 so that the tip of the discharge electrode 2 faces the collection electrode 1. The shape of the support member 43 is not particularly limited insofar as the collection electrode 1 and the discharge electrode 2 can be disposed opposite to each other at a given interval. As shown in FIG. 6, the support member 43 preferably have a shape in which a thin cylindrical portion 48 (small-diameter portion) is connected to one end of a thick cylindrical portion 47 (large-diameter portion), wherein the end face of the large-diameter portion 47 connected to the small-diameter portion 48 serves as the support stage 42, the laminate 44 is embedded in the support stage 42, and the end of the small-diameter portion 48 serves as the end 41.

The size of the support member 43 is not particularly limited insofar as the discharge electrode and the collection electrode can be disposed at the desired distance, the collection electrode can have the desired area, and the flow of exhaust gas is not unnecessarily hindered when the particulate matter detection device is installed in an exhaust pipe. For example, the length of the support member 43 is preferably 10 to 55 mm, and the diameter of the cross section of the support member 43 perpendicular to the lengthwise direction (i.e., the diameter of the cross section of the large-diameter portion 47 perpendicular to the axial direction in the case of the support member 43 shown in FIG. 6) is preferably 8 to 30 mm. When the cross section of the support member 43 perpendicular to the axial direction is not circular, it is preferable that the support member 43 have a diameter so that the area of the support member 43 is almost equal to that when the support member 43 has a circular cross section and the above-mentioned diameter. It is preferable that the diameter of the cross section of the small-diameter portion 48 perpendicular to the axial direction be about 20 to 70% of the diameter of the cross section of the large-diameter portion 47 perpendicular to the axial direction. It is preferable that the small-diameter portion 48 is disposed at a position near the periphery of the end of the large-diameter portion 47 or disposed to be inscribed to the periphery of the end of the large-diameter portion 47. This makes it possible to form a large support stage 42. The support member 43 shown in FIG. 6 is configured so that the support stage 42 is inclined with respect to the direction that extends from the discharge electrode 2 to the support stage 42.

Note that the support stage 42 may be perpendicular to the direction that extends from the discharge electrode 2 to the support stage 42. The particulate matter can be steadily collected and detected in an exhaust pipe by disposing the laminate 44 and the discharge electrode 2 on the support member 43 so that the amount of particulate matter contained in the exhaust gas can be measured. FIG. 6 is a perspective view schematically showing a state in which the laminate (e.g., collection electrode) and the discharge electrode are disposed on the support member.

It is preferable to form folds 45 between the end 41 and the support stage 42 (i.e., in the small-diameter portion 48) on the support member 43 so that a creeping discharge does not occur on the surface of the support member 43 (particularly the surface of the small-diameter portion 48 when the support member 43 has a shape shown in FIG. 6) when applying a high voltage between the collection electrode 1 and the discharge electrode 2. It is preferable that lines which are connected to each electrodes (e.g., collection electrode 1) are introduced into the support member 43 from a rear end 46 (i.e., the end of the large-diameter portion 47 that is not connected to the small-diameter portion 48), and connected to each electrodes inside the support member 43. The material for the support member 43 is not particularly limited, but is preferably a ceramic. It is more preferable that the material for the support member 43 contain at least one component selected from the group consisting of alumina, magnesium oxide, silicon oxide, silicon nitride, aluminum nitride, zirconia, cordierite, mullite, spinel, a magnesium-calcium-titanium oxide, a barium-titanium-zinc oxide, and a barium-titanium oxide. The support member 43 may be secured on an exhaust pipe or the like by an arbitrary method insofar as vibrations or the like that hinder the measurement do not occur during use, or the support member 43 is not removed from an exhaust pipe. For example, the support member 43 may be secured on a threaded socket that is made of stainless steel (SS) or the like and is provided with a connector having a mechanism for connecting an electric wire or the like to the rear end 46, and the socket may be screwed into an exhaust pipe. This makes it possible to easily install the support member 43. In this case, it is preferable that the rear end 46 have a circular shape.

(2) Method of Producing Particulate Matter Detection Device

A method of producing the particulate matter detection device according to one embodiment of the present invention is described below.

(2-1) Preparation of Dielectric-Forming Raw Material

A ceramic raw material that contains at least one component selected from the group consisting of alumina, magnesium oxide, silicon oxide, silicon nitride, aluminum nitride, zirconia, a cordierite-forming raw material, mullite, spinel, a magnesium-calcium-titanium oxide, a barium-titanium-zinc oxide, and a barium-titanium oxide is mixed with other components to prepare a forming raw material (dielectric-forming raw material) in the form of a slurry. Note that the ceramic raw material is preferably but not limited to the above-mentioned components. As the components other than the ceramic raw material, it is preferable to use a binder, a plasticizer, a dispersant, and a solvent (e.g., water or organic solvent). The inter-electrode dielectric and the back-side dielectric are formed using the dielectric-forming raw material. The inter-electrode dielectric and the back-side dielectric may be formed using an identical dielectric-forming raw material, or may be formed using dielectric-forming raw materials that differ in composition.

The binder is not particularly limited. An aqueous binder or a non-aqueous binder may be used. As the aqueous binder, methyl cellulose, polyvinyl alcohol, polyethylene oxide, or the like may be suitably used. As the non-aqueous binder, polyvinyl butyral, an acrylic resin, polyethylene, polypropylene, or the like may be suitably used. Examples of the acrylic resin include a (meth)acrylic resin, a (meth)acrylate copolymer, an acrylate-methacrylate copolymer, and the like.

The binder is preferably added in an amount of 3 to 20 parts by mass, and more preferably 6 to 17 parts by mass, based on 100 parts by mass of the ceramic raw material. If the amount of the binder is within the above range, cracks or the like can be prevented when forming the forming raw material in the form of a slurry to produce a green sheet, or when drying and firing the green sheet.

As the plasticizer, glycerol, polyethylene glycol, dibutyl phthalate, di(2-ethylhexyl)phthalate, diisononyl phthalate, or the like may be used.

The plasticizer is preferably added in an amount of 30 to 70 parts by mass, and more preferably 45 to 55 parts by mass, based on 100 parts by mass of the binder. If the amount of the plasticizer is more than 70 parts by mass, the resulting green sheet becomes too soft and may be deformed when processing the green sheet. If the amount of the plasticizer is less than 30 parts by mass, the resulting green sheet becomes too hard so that the handling capability may deteriorate (e.g., cracks may occur when merely bending the green sheet).

As the dispersant, an aqueous dispersant (e.g., anionic surfactant, wax emulsion, or pyridine) or a non-aqueous dispersant (e.g., fatty acid, phosphate, or synthetic surfactant) may be used.

The dispersant is preferably added in an amount of 0.5 to 3 parts by mass, and more preferably 1 to 2 parts by mass, based on 100 parts by mass of the ceramic raw material. If the amount of the dispersant is less than 0.5 parts by mass, the dispersibility of the ceramic raw material may decrease. As a result, the green sheet may produce cracks or the like. If the amount of the dispersant is more than 3 parts by mass, the amount of impurities may increase during firing although the dispersibility of the ceramic raw material remains the same.

Examples of the organic solvent include xylene, butanol, and the like. The organic solvents may be used either individually or in combination. The solvent is preferably added in an amount of 50 to 200 parts by mass, and more preferably 75 to 150 parts by mass, based on 100 parts by mass of the ceramic raw material.

The above-mentioned materials are sufficiently mixed using an alumina pot and alumina cobblestone to prepare a forming raw material slurry for forming a green sheet. The forming raw material slurry may be prepared by mixing the materials by ball milling using a mono ball.

The resulting forming raw material slurry is stirred under reduced pressure to remove bubbles, and the viscosity of the forming raw material slurry is adjusted to a predetermined value. The viscosity of the forming raw material slurry thus prepared is preferably 2.0 to 6.0 Pa·s, more preferably 3.0 to 5.0 Pa·s, and particularly preferably 3.5 to 4.5 Pa·s. The slurry can be easily formed into a sheet by adjusting the viscosity of the slurry within the above range. It may be difficult to form the slurry into a sheet if the viscosity of the slurry is too high or too low. The viscosity of the slurry refers to a value measured using a B type viscometer.

(2-2) Forming

The forming raw material slurry obtained by the above method is formed into a sheet to obtain a green sheet for forming the inter-electrode dielectric or the back-side dielectric. The forming method is not particularly limited insofar as a green sheet can be formed by forming the forming raw material into a sheet. A doctor blade method, a press forming method, a rolling method, a calender roll method, or the like which is known in the art may be used.

The thickness of the green sheet is preferably 50 to 800 µm.

The electrode (collection electrode and measurement electrode), line, and heater are disposed on the surface of the resulting green sheet. For example, when producing the particulate matter detection device shown in FIG. 1, it is preferable to print the electrodes, lines (not shown), and heater at a corresponding position of the green sheet so that each electrodes, lines, and heater are disposed at a predetermined position. In this case, a conductive paste for forming the electrodes, lines, and heater is prepared. The conductive paste may be prepared by adding a binder and a solvent (e.g., terpineol) to a powder that contains at least one component selected from the group consisting of gold, silver, platinum, nickel, molybdenum, and tungsten, and sufficiently kneading the mixture using a triple roll mill or the like. It is preferable to use platinum for the conductive paste for forming the heater. The conductive paste thus prepared is printed on the surface of the green sheet by screen printing or the like to form the electrode and the line having a predetermined shape. The measurement electrode 5 may be printed on the green sheet for forming the inter-electrode dielectric 4, or may be printed on the green sheet for forming the back-side dielectric 6.

The green sheets are then stacked. The green sheets are stacked so that the electrode and heater are disposed as shown in FIG. 1. The green sheets are preferably stacked while applying a pressure.

It is preferable to form the heat insulator by further stacking the green sheet. When forming a porous heat insulator, it is preferable to add a foaming agent to the slurry for green sheet, form the slurry into a sheet, and stack the resulting sheet. In this case, since the heat insulator 8 and the dielectric 6 are easily separated during firing, it is important to carefully set the thickness of the heat insulator, the amount of the foaming agent, and the stacking pressure.

(2-3) Firing

The resulting green sheet laminate is dried at 60 to 150° C., and fired at 1200 to 1600° C. to obtain a laminate that includes a collection electrode, an inter-electrode dielectric, a measurement electrode, a back-side dielectric, and a heater that form a particulate matter detection device. When the green sheet contains an organic binder, it is preferable to degrease the green sheet at 400 to 800° C. before firing.

(2-4) Discharge Electrode

It is preferable to use a wire-shaped electrode that contains an Ni alloy as a matrix as the discharge electrode. The wire is preferably obtained by forming a wire rod by wire drawing, and slicing the wire rod by electrical discharge machining or cutting the wire rod using a blade. It is preferable to weld a noble metal containing Pt that exhibits durability as the main component to the end (discharge section) of the discharge electrode.

(2-5) Support Member

The support member is preferably formed of a ceramic sintered body (e.g., alumina or aluminum nitride). It is preferable to form a hole in the support member in the axial direction toward the discharge electrode. The wire that forms the discharge electrode is inserted into the hole. It is preferable to form folds or the like on the support member by cutting work or the like. For example, the support member is preferably formed to have a shape similar to that of the support member 43 shown in FIG. 6.

(2-6) Discharge Power Supply

The discharge power supply is preferably a power supply that includes one-transistor flyback step-up power supply having a simple circuit configuration and a rectifier circuit.

(2-7) Measurement Section

As the measurement section, it is preferable to use an LCR meter that calculates the impedance from the applied voltage and the measured current, for example.

(2-8) Heater Power Supply

As the heater power supply, it is preferable to use a step-down chopper switching power supply using a self-arc-extinguishing semiconductor switch. It is more preferable to use a power supply that calculates the temperature of the heater from the heater voltage and current and has a temperature control function.

(2-9) Production of Particulate Matter Detection Device

It is preferable to secure the laminate and the discharge electrode on the support member so that the end of the discharge electrode faces the collection electrode of the laminate. For example, it is preferable to form the support member 43 shown in FIG. 6, mount the discharge electrode 2 on the end 41, and mount the laminate 44 on the support stage 42. It is preferable to connect the discharge power supply 9 to the collection electrode 1 and the discharge electrode 2 through the resistor 13 shown in FIG. 1. It is preferable to connect the measurement section to the collection electrode and the measurement electrode, and connect the heater power supply to the heater. The particulate matter detection device according to this embodiment can be produced in this manner.

(Second Invention)

(3) Particulate Matter Detection Method

A particulate matter detection method according to one embodiment of the present invention is described below.

The particulate matter detection method according to this embodiment includes a charging-collection step that charges particulate matter contained in gas by utilizing a corona discharge, and collects the charged particulate matter by a collection electrode by utilizing an electrostatic force, and a measurement step that detects a change in the impedance between the collection electrode that has collected the particulate matter and a measurement electrode to detect the particulate matter contained in the gas. Since the particulate matter detection method according to this embodiment can detect the particulate matter by detecting a change of the impedance between the collection electrode and the measurement electrode due to the collected particulate matter, the particulate matter can be simply detected while reducing a measurement error.

The charging-collection step and the measurement step included in the particulate matter detection method according to this embodiment are preferably carried out using the particulate matter detection device according to the present invention. It is preferable to install the particulate matter detection device according to the present invention in an exhaust pipe of a diesel engine or the like, charge and collect the particulate matter, and detect a change in impedance to detect the particulate matter contained in the gas (exhaust gas) inside the exhaust pipe. It is preferable that a specific embodiment and usage of each element of the particulate matter detection device used for the particulate matter detection method according to this embodiment is the same as a specific embodiment and usage of each element of the particulate matter detection device according to the present invention.

(3-1) Charging-Collection Step

The charging-collection step includes charging the particulate matter contained in the gas by utilizing a corona discharge, and collecting the charged particulate matter by the collection electrode by utilizing an electrostatic force. The method of charging the particulate matter by utilizing a corona discharge is not particularly limited. It is preferable to charge the particulate matter contained in the gas by utilizing a corona discharge that occurs when applying a high voltage between the discharge electrode and the collection electrode of the particulate matter detection device according to the present invention. The method of collecting the charged particulate matter by the collection electrode by utilizing an electrostatic force is not particularly limited. Since a high voltage is applied between the discharge electrode and the collection electrode when using the particulate matter detection device according to the present invention, the charged particulate matter is collected by the collection electrode having a different polarity due to the electrostatic force.

(3-2) Measurement Step

The measurement step includes detecting a change in the impedance between the collection electrode that has collected the particulate matter and the measurement electrode to detect the particulate matter contained in the gas. The method of detecting a change in the impedance between the collection electrode and the measurement electrode is not particularly limited. It is preferable to detect a change in impedance by measuring the alternating-current impedance, the capacitance, or the like between the collection electrode and the measurement electrode using the measurement section of the particulate matter detection device according to the present invention.

(3-3) Cleaning of Collection Electrode

In the particulate matter detection method according to this embodiment, it is preferable to detect the particulate matter using the particulate matter detection device according to the present invention that includes the heater for oxidizing and removing the collected particulate matter. This aims at further detecting the particulate matter after oxidizing and removing the particulate matter collected by the collection electrode using the heater. The particulate matter detection device according to the present invention that is configured so that the particulate matter is oxidized and removed by causing a creeping discharge using the collection electrode may also be used. The particulate matter can be steadily detected for a long period of time by repeating a cycle that includes oxidizing and removing the particulate matter collected by the collection electrode, detecting the particulate matter, and then oxidizing and removing the particulate matter.

(3-4) Particulate Matter Detection Cycle

In the particulate matter detection method according to this embodiment, it is preferable not to detect a change in impedance when charging the particulate matter by utilizing a corona discharge and collecting the charged particulate matter by the collection electrode, and not to cause a corona discharge when detecting a change in impedance after collecting the particulate matter by the collection electrode. It is preferable to oxidize and remove the collected particulate matter using the heater or by a creeping discharge using the collection electrode after detecting a change in the impedance between the collection electrode and the measurement electrode. It is preferable to then charge the particulate matter by utilizing a corona discharge and collect the charged particulate matter by the collection electrode.

In the particulate matter detection method according to this embodiment, when detecting the particulate matter using the particulate matter detection device according to the present invention, it is preferable to stop applying a high voltage between the collection electrode and the discharge electrode so that a corona discharge does not occur when detecting a change in the impedance between the collection electrode and the measurement electrode. If a change in the impedance between the collection electrode and the measurement electrode is detected in a state in which a high voltage is applied between the collection electrode and the discharge electrode, a change in impedance may not be steadily and accurately detected since the collected particulate matter is charged. Therefore, it is preferable to repeat a cycle that includes applying a high voltage between the collection electrode and the discharge electrode for a given period of time or under given conditions so that a corona discharge occurs, detecting a change in the impedance between the collection electrode and the measurement electrode without causing a corona discharge, burning and removing the particulate matter collected by the collection electrode without detecting a change in impedance, and then causing a corona discharge.

Figure 7:
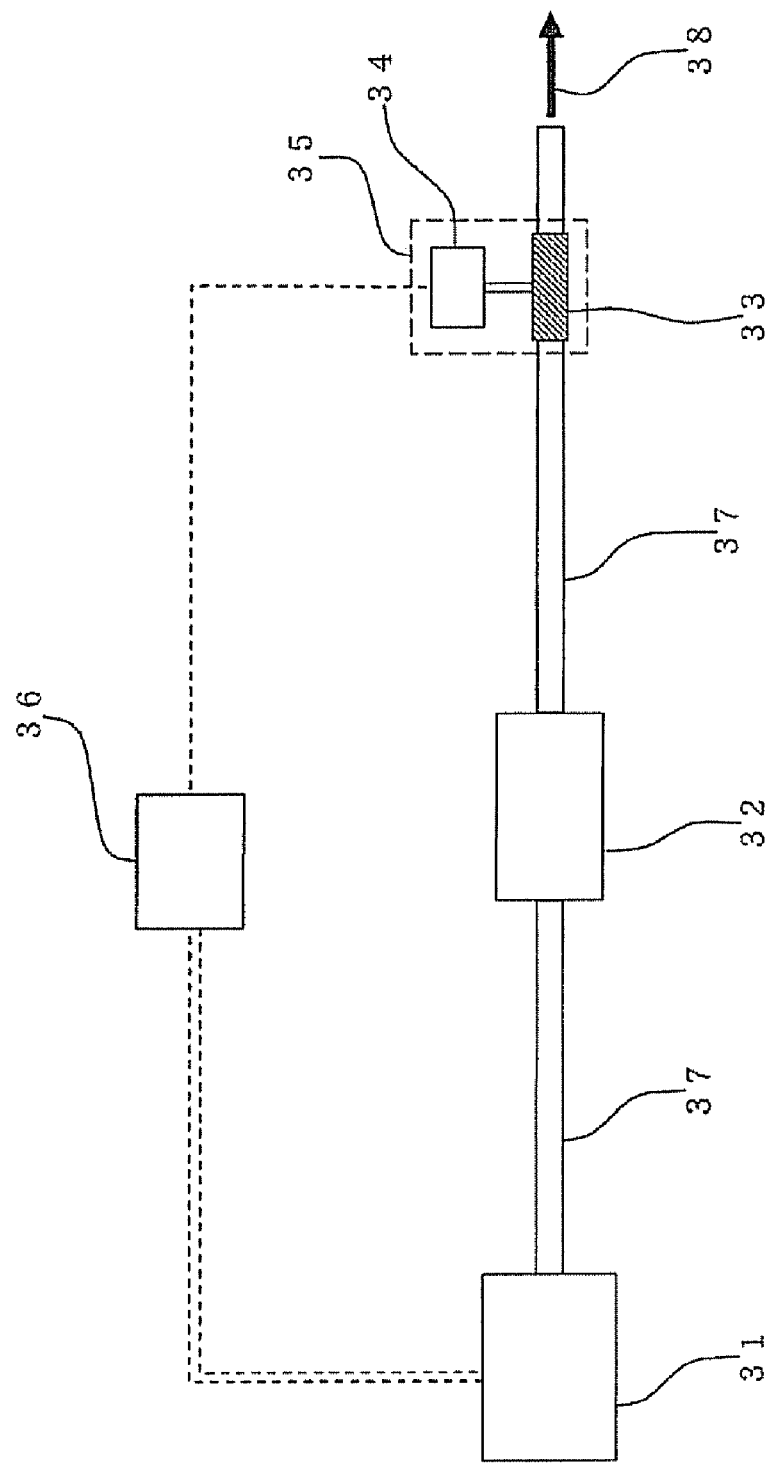
FIG. 7 is a perspective view schematically showing a state in which a particulate matter detection device according to one embodiment of the present invention is installed in an exhaust pipe of a diesel engine on the downstream side of a purification device.

As shown in FIG. 7, when a particulate matter detection device 35 according to this embodiment is installed in an exhaust pipe 37 of an automotive diesel engine 31, for example, it is preferable to cause a corona discharge when the engine speed, torque, and the like of the diesel engine 31 and the flow rate, the temperature, and the like of an exhaust gas 38 have satisfied given conditions. FIG. 7 is a schematic view showing a state in which the particulate matter detection device 35 according to this embodiment is installed in the exhaust pipe 37 of the diesel engine 31 on the downstream side of a purification device 32. The particulate matter detection device 35 includes a charging-collection section 33 that includes the collection electrode 1, the discharge electrode 2, and the like, and a sensor circuit 34 that includes the measurement section, the power supply, and the like, for example. As shown in FIG. 7, the engine speed, torque, and the like of the diesel engine 31 and the flow rate, the temperature, and the like of the exhaust gas 38 may be transmitted to a calculation section 36 from the diesel engine 31 and the like, and the calculation section 36 may instruct the sensor circuit 34 to cause a corona discharge and collect the particulate matter when the calculation section 36 has determined that the given conditions have been satisfied. It is preferable to terminate the corona discharge after causing the corona discharge and collecting the particulate matter, detect a change in the impedance between the collection electrode and the measurement electrode, and then transmit the data to the calculation section 36 so that the calculation section 36 calculates the amount of particulate matter contained in the exhaust gas and the like.

When the calculation section 36 calculates the amount of particulate matter contained in the exhaust gas and the like, it is preferable to transmit data that indicates the amount of collected particulate matter (g/s)(x) obtained by detecting a change in impedance to the calculation section 36, and cause the calculation section 36 to perform calculations indicated by "$y = x \cdot (1 - \text{Exp}(-wd \cdot A/Q)^k)$" to calculate the amount of particulate matter (g/s)(y). Note that "A" indicates a sensor head area ($m^2$), "Q" indicates an actual exhaust gas flow rate ($m^3/s$), "wd" indicates a particle drift velocity, and "k" indicates a correction coefficient obtained by experiments.

The period of time in which the particulate matter is charged by utilizing a corona discharge and collected by the collection electrode in the charging-collection step is preferably 1 to 60 seconds, and more preferably 2 to 10 seconds. If the period of time is less than 1 second, the measurement accuracy of the amount of particulate matter may decrease due to a decrease in the amount of particulate matter collected. If the period of time is more than 60 seconds, since the amount of particulate matter collected increases, it may be difficult to accurately determine the amount of particulate matter collected by detecting a change in impedance.

The period of time in which a change in impedance is detected in the measurement step is about 1 to 60 seconds.

The period of time in which the particulate matter is oxidized and removed using the heater is preferably 1 to 120 seconds, and more preferably 3 to 30 seconds. If the period of time is less than 1 second, the particulate matter may not be sufficiently oxidized and removed. If the period of time is more than 120 seconds, unnecessary energy consumption may occur. The period of time in which the particulate matter is oxidized and removed by causing a creeping discharge is preferably 1 to 120 seconds, and more preferably 3 to 30 seconds. If the period of time is less than 1 second, the particulate matter may not be sufficiently oxidized and removed. If the period of time is more than 120 second, unnecessary energy consumption may occur.

(Third Invention)

(4) Particulate Matter Detection Device

Figure 8:
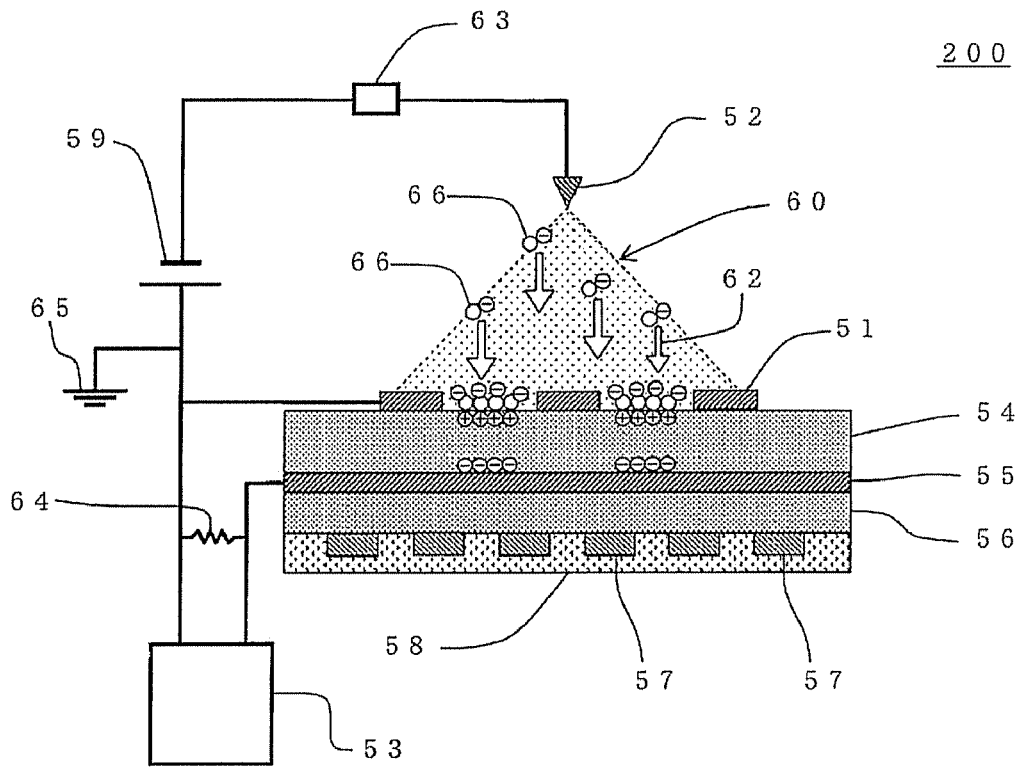
FIG. 8 is a cross-sectional view schematically showing a particulate matter detection device according to one embodiment of the present invention.

FIG. 8 is a cross-sectional view schematically showing a particulate matter detection device according to one embodiment of the present invention (third invention). As shown in FIG. 8, a particulate matter detection device 200 according to this embodiment includes a dielectric (inter-electrode dielectric) 54, a collection electrode 51 that is disposed on one side of the inter-electrode dielectric 54, a measurement electrode 55 that is disposed on the other side of the inter-electrode dielectric 54, a discharge electrode 52 that allows a corona discharge to occur when a voltage is applied between the collection electrode 51 and the discharge electrode 52, and a measurement section 53 that detects the voltage between the collection electrode 51 and the measurement electrode 55. The particulate matter detection device 200 according to this embodiment is disposed in a gas passage that allows gas containing particulate matter to pass through and detects the particulate matter contained in the gas, the particulate matter detection device 200 detecting the particulate matter by charging the particulate matter contained in the gas by utilizing a corona discharge, collecting the charged particulate matter by the collection electrode 51 by utilizing an electrostatic force, and detecting the voltage between the collection electrode 51 that has collected the particulate matter and the measurement electrode 55 using the measurement section 53. It is preferable to detect the particulate matter by calculating the amount of particulate matter from the difference between the voltage between the collection electrode and the measurement electrode when the particulate matter is absent and the voltage between the collection electrode and the measurement electrode when the particulate matter has been collected by the collection electrode. The particulate matter detection device according to this embodiment can detect the particulate matter by a very simple voltage measurement. Moreover, since detection of the particulate matter is affected to only a small extent by the impedance of a support member, a cable, or the like, a measurement error can be further reduced as compared with the case of measuring the impedance (first invention). It is also possible to detect the particulate matter while collecting the particulate matter.

Figure 9:
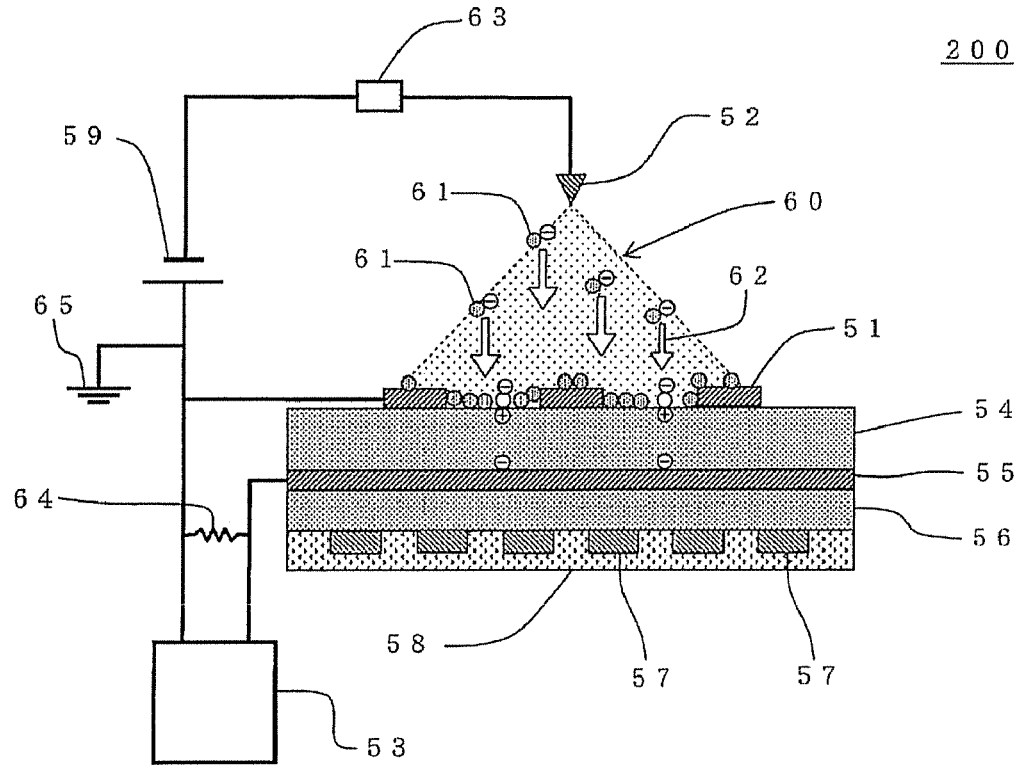
FIG. 9 is a perspective view schematically showing a particulate matter detection device according to one embodiment of the present invention.

In the particulate matter detection device 200 according to this embodiment, as shown in FIG. 8, when a corona discharge has occurred in a state in which the particulate matter is absent, ions 66 and the like produced in air due to a corona discharge 60 are drawn toward to the collection electrode 51 due to an electrostatic force, and adhere to the surface of the inter-electrode dielectric 54. This causes the inter-electrode dielectric 54 to undergo polarization so that a potential difference occurs between the collection electrode 51 and the measurement electrode 55. In this case, the side of the inter-electrode dielectric 54 to which the ions 66 and the like adhere is positively charged, and the other side of the inter-electrode dielectric 54 is negatively charged. As shown in FIG. 9, when a corona discharge has occurred in a state in which the particulate matter is present, charged particulate matter 61 is drawn toward to the collection electrode 51 due to an electrostatic force, and adheres to the surfaces of the collection electrode 51 and the inter-electrode dielectric 54. As a result, since the amount of ions and the like that adhere to the surface of the inter-electrode dielectric 54 decreases so that the inter-electrode dielectric 54 undergoes polarization to only a small extent, the potential difference between the collection electrode 51 and the measurement electrode 55 decreases. Therefore, since the potential difference between the collection electrode 51 and the measurement electrode 55 differs between the case where a corona discharge has occurred in a state in which the particulate matter is absent and the case where a corona discharge has occurred in a state in which the particulate matter is present, the particulate matter can be detected by measuring the voltage between the collection electrode 51 and the measurement electrode 55 in each state that changes due to collection of the particulate matter.

In the particulate matter detection device 200 according to this embodiment, a discharge power supply 59 is connected to the collection electrode 51 and the discharge electrode 52 to form a high-voltage circuit, as shown in FIG. 9. A high voltage is applied between the collection electrode 51 and the discharge electrode 52 from the discharge power supply 59 so that the corona discharge 60 occurs. Specifically, when a high voltage is applied, a corona discharge occurs between the discharge electrode 52 and the collection electrode 51 that serves as an opposite electrode (positive electrode). When the particulate matter passes through the area in which the corona discharge 60 occurs, the particulate matter is negatively charged due to the corona discharge. The charged particulate matter 61 is drawn toward the collection electrode 51 having an opposite polarity (positive electrode) due to an electrostatic force, and is collected by the collection electrode 51. As shown in FIG. 8, when a corona discharge has occurred in a state in which the particulate matter is absent, the ions 66 and the like are produced in air, and drawn toward to the collection electrode due to an electrostatic force instead of the charged particulate matter. An arrow 62 shown in FIGS. 8 and 9 indicates a state in which the negatively charged particulate matter 61 and the ions 66 are subjected to an electrostatic force in the direction indicated by the arrow 62. When the particulate matter is charged by utilizing a corona discharge and collected by utilizing an electrostatic force, the amount of particulate matter collected increases as the amount of particulate matter contained in the gas increases, and decreases as the amount of particulate matter contained in the gas decreases. The voltage between the collection electrode 61 and the measurement electrode 65 to be detected varies depending on the amount of particulate matter collected. Therefore, the amount of particulate matter contained in the gas can be measured by detecting a change in the voltage between the collection electrode 61 and the measurement electrode 65 to detect the amount of particulate matter collected. In order to determine the amount of particulate matter collected, it is preferable to measure the voltage between the collection electrode and the measurement electrode in a state in which the particulate matter is absent in advance, and determine the relationship between the amount of particulate matter collected and the voltage to create a calibration curve. FIG. 9 is a cross-sectional view schematically showing the particulate matter detection device according to one embodiment of the present invention.

The distance between the collection electrode 51 and the discharge electrode 52 is preferably 5 to 50 mm, and more preferably 10 to 40 mm. If the distance between the collection electrode 51 and the discharge electrode 52 is within the above range, a corona discharge occurs more efficiently so that the particulate matter can be sufficiently collected. If the distance between the collection electrode 51 and the discharge electrode 52 is less than 5 mm, the measurement accuracy may decrease due to a decrease in collection rate. If the distance between the collection electrode 51 and the discharge electrode 52 is more than 50 mm, a higher voltage may be required (i.e., energy may be unnecessarily consumed). Note that the distance between the collection electrode 51 and the discharge electrode 52 refers to the radius of a virtual sphere that is drawn around the tip of the discharge electrode 52 and comes in contact with only part of the collection electrode.

It is preferable that the discharge power supply 59 shown in FIGS. 8 and 9 is a power supply that can supply a stable direct-current voltage that allows a corona discharge to occur between the collection electrode 51 and the discharge electrode 52. For example, the discharge power supply is preferably a power supply (discharge power supply) using a flyback power supply circuit or the like that stores energy from an input-side power supply in a transformer and discharges the stored energy to the output side to supply a high direct-current voltage. In the flyback power supply circuit, storage and discharge of energy into and from the transformer are controlled by a transistor or the like, and the output-side current is rectified by a diode. The voltage applied between the collection electrode 51 and the discharge electrode 52 is preferably 2 to 10 kV (DC), and more preferably 5 to 8 kV (DC). If the voltage applied between the collection electrode 51 and the discharge electrode 52 is lower than 5 kV, a corona discharge may occur to only a small extent. If the voltage applied between the collection electrode 51 and the discharge electrode 52 is higher than 10 kV, an ark discharge may occur or a creeping discharge may occur on the surface of another member or the like. The current that flows between the collection electrode 51 and the discharge electrode 52 (corona discharge current) is preferably 1 mA or less, and more preferably 1 to 100 μA. If the current is less than 1 μA, the collection rate may decrease. It is desirable to reduce power consumption since it directly affects fuel consumption. The amount of power consumed by the power supply is preferably 10 W or less, and more preferably 1 W or less, talking account of a reduction in electromagnetic noise and the size of the circuit that causes a corona discharge. In the high-voltage circuit, the discharge power supply 59 is preferably connected to the discharge electrode 52 via a resistor 63. The resistor 63 is used as a limiting resistor that limits a current that flows between the discharge electrode 52 and the collection electrode 51 when the impedance between the discharge electrode 52 and the collection electrode 51 has decreased so that an arc discharge does not occur between the discharge electrode 52 and the collection electrode 51. Therefore, the resistor 63 preferably has a resistance of 500 kΩ to 20 MΩ, for example.

The voltage between the collection electrode 51 and the measurement electrode 55 varies depending on the corona discharge conditions and resistance of the resistor connected between the collection electrode 51 and the measurement electrode 55. The voltage between the collection electrode 51 and the measurement electrode 55 is preferably 36 V or less so that an analog IC (e.g., operational amplifier) can be used.

The discharge electrode 52 is preferably an electrode of which the end is formed at an acute angle. For example, the discharge electrode 52 preferably has a sharp end (e.g., in the shape of a needle, a rod, or a plate) so that electric field concentration occurs.

The collection electrode 51 serves as an opposite electrode of the discharge electrode 52 so that a corona discharge occurs, and also serves as a collection member (electrode) that collects the charged particulate matter.

Figure 10A:
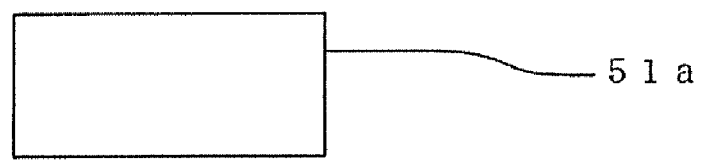
FIG. 10A is a plan view schematically showing the shape of a collection electrode.
Figure 10B:
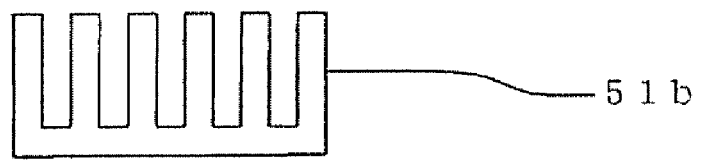
FIG. 10B is a plan view schematically showing the shape of a collection electrode.
Figure 10C:
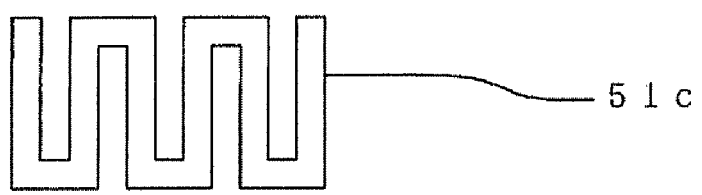
FIG. 10C is a plan view schematically showing the shape of a collection electrode.

The collection electrode may be a plate-shaped electrode (collection electrode 51a) that has a rectangular external profile, as shown in FIG. 10A. Note that it is preferable that the collection electrode is a plate-shaped electrode that has an external profile provided with elevations or depressions, as shown in FIGS. 10B and 10C. Note that the expression "provided with elevations or depressions" used herein refers to a case where the external profile is provided with both elevations and depressions, a case where the external profile is provided with only depressions, and a case where the external profile is provided with only elevations. FIGS. 10A, 10B, and 10C are plan views schematically showing the collection electrode. A collection electrode 51a shown in FIG. 10B differs from the rectangular collection electrode shown in FIG. 10A in that one side of the collection electrode 51b is provided with a plurality of depressions and elevations. In other words, a plurality of elevations are formed in FIG. 10B in a comb-like configuration. Specifically, the terms "depression" and "elevation" may be interchangeably used. Such a case is also included within the scope of the expression "provided with elevations or depressions." A collection electrode 51c shown in FIG. 10C differs from the rectangular collection electrode shown in FIG. 10A in that two parallel sides of the collection electrode are alternately provided with a plurality of depressions. Note that the collection electrode may have a shape in which the external profile is rectangular and is not provided with depressions and elevations and one or more slits (which is formed in a state where outer edge is remained) are formed inside the outer edge. The external profile is not limited to a rectangle, but may be a polygon (e.g., pentagon), a circle, an oval, a track, or the like. Alternatively, the collection electrode may have a shape in which the external profile is provided with depressions and elevations and one or more slits are formed inside the outer edge. The collection electrode 51 of the particulate matter detection device 200 shown in FIGS. 8 and 9 has a comb-like configuration (see FIG. 10B). FIGS. 8 and 9 show the cross section of the collection electrode 51 perpendicular to the direction in which the plurality of elevations extend.

The thickness of the collection electrode 51 is not particularly limited insofar as the collection electrode 51 exhibits sufficient durability and does not hinder the flow of exhaust gas. The area of the collection electrode 51 is not particularly limited insofar as the voltage sufficiently changes when the collection electrode 5 has collected the particulate matter, and electric power is not unnecessarily consumed when cleaning the adhering particulate matter. The size of the collection electrode 51 is not particularly limited, but is preferably 900 mm$^2$ or less. The number of collection electrodes 51 is not particularly limited. An arbitrary number of collection electrodes 51 may be provided.

It is preferable that the material for each of the collection electrode 51 and the discharge electrode 52 contain at least one component selected from the group consisting of gold, silver, platinum, nickel, molybdenum, stainless steel, and tungsten. The content of these components is preferably 20 vol % or more, and more preferably 60 vol % or more.

As shown in FIGS. 8 and 9, the particulate matter detection device 200 according to this embodiment includes the dielectric (inter-electrode dielectric) 54, the collection electrode 51 that is disposed on one side of the inter-electrode dielectric 54, and the measurement electrode 55 that is disposed on the other side of the inter-electrode dielectric 54. The measurement section 53 is connected to the collection electrode 51 and the measurement electrode 55, and the measurement section 53 detect a change in the voltage between the collection electrode 51 and the measurement electrode 55 to detect the particulate matter. A line connected to the collection electrode 51 is connected to a ground 65. The particulate matter can be detected with high sensitivity without being affected by the outside environment and requiring a special measurement device and operation by measuring a change in the voltage between the collection electrode 51 and the measurement electrode 55. The measurement can be continuously performed while collecting the particulate matter. Moreover, the particulate matter detection device 200 can be reduced in size and produced inexpensively.

The distance between the collection electrode 51 and the measurement electrode 55 is not particularly limited insofar as a change in voltage due to the particulate matter collected by the collection electrode 51 can be accurately detected. The distance is preferably 10 to 5000 μm, and more preferably 50 to 1000 μm, for example. A change in the voltage between the collection electrode 51 and the measurement electrode 55 can be more accurately determined if the distance is within the above range. Since the distance between the collection electrode 51 and the discharge electrode 52 is equal to the thickness of the inter-electrode dielectric 54, it is preferable to set the thickness of the inter-electrode dielectric 54 within the above range.

The capacitance between the collection electrode 51 and the measurement electrode 55 when the particulate matter is not collected is preferably 0.01 to 100 pF (picofarad), and more preferably 0.1 to 10 pF. If it is less than 0.01 pF, a change in voltage due to adhesion of the charged particles may increase so that the sensitivity may increase too much. If it is more than 100 pF, a change in voltage due to adhesion of the charged particles may decrease so that the sensitivity may decrease too much.

The measurement electrode 55 is not particularly limited insofar as the voltage caused by polarization of the inter-electrode dielectric 54 can be accurately detected by the measurement section 53. It is preferable that the measurement electrode 55 have a size almost equal to the size (area) of the external profile of the collection electrode 51 (on the assumption that elevations and depressions are not formed), for example. It is preferable that the measurement electrode 55 is disposed at such a position that the entire collection electrode 51 overlaps the measurement electrode 55 when moving the collection electrode 51 in the direction normal to the collection electrode 51. The thickness of the measurement electrode 55 is not particularly limited, but is preferably 5 to 100 μm, and more preferably 10 to 50 μm, for example. It is preferable that the material for the measurement electrode 55 contain at least one component selected from the group consisting of gold, silver, platinum, nickel, molybdenum, stainless steel, and tungsten. The content of these components is preferably 20 vol % or more, and more preferably 60 vol % or more.

The material for the inter-electrode dielectric 54 is not particularly limited, but is preferably a ceramic. It is more preferable that the material for the inter-electrode dielectric 4 contain at least one component selected from the group consisting of alumina, magnesium oxide, silicon oxide, silicon nitride, aluminum nitride, zirconia, cordierite, mullite, spinel, a magnesium-calcium-titanium oxide, a barium-titanium-zinc oxide, and a barium-titanium oxide. Among these, alumina and aluminum nitride are particularly preferable. A dielectric containing such a compound exhibits stable electrical characteristics (e.g., dielectric constant and insulation resistance) at a high temperature, and rarely breaks even if a change in temperature occurs (i.e., exhibits excellent thermal impact resistance). The relative dielectric constant of the inter-electrode dielectric 54 is preferably 1 to 100, and more preferably 4 to 100. If the dielectric constant of the inter-electrode dielectric 54 is within the above range, a stable measurement can be performed without being affected by a disturbance (e.g., small leakage current) due to a decrease in impedance.

It is preferable that the inter-electrode dielectric 54 is a sheet-shaped dielectric (see FIG. 8). The shape of the planar portion of the sheet-shaped dielectric is not particularly limited. The shape of the planar portion of the sheet-shaped dielectric may be a polygon (e.g., quadrangle), a circle, an oval, or the like. The size of the inter-electrode dielectric 54 is not particularly limited, but is preferably about 1 to 100 mm$^2$. The thickness of the inter-electrode dielectric 54 is not particularly limited, but is preferably 1 to 2000 μm, and more preferably 10 to 1000 μm (i.e., the preferable distance between the collection electrode 51 and the measurement electrode 55).

It is preferable that the measurement section 53 is a voltmeter that can measure the voltage between the collection electrode 51 and the measurement electrode 55. It is preferable that the voltmeter have an excellent response capability. As shown in FIGS. 8 and 9, it is preferable that a resistor 64 is connected in parallel with the voltmeter in order to accurately measure the voltage between the collection electrode 51 and the measurement electrode 55. It is preferable that the resistor 64 have a resistance of 100 MΩ or less. The resistor 64 is preferably a metal film resistor or the like.

As shown in FIGS. 8 and 9, it is preferable that the particulate matter detection device 200 according to this embodiment further include a dielectric (back-side dielectric) 56 that is disposed on the side (back side) of the measurement electrode 55 opposite to the side on which the inter-electrode dielectric 54 is disposed, and a heater 57 disposed on the surface of the back-side dielectric 56 (i.e., the side opposite to the side on which the measurement electrode 55 is disposed). It is preferable that a heater power supply (not shown) is connected to the heater 57, and the particulate matter collected by the collection electrode 51 is oxidized and removed by heat generated by the heater 57 by heating the heater 57 by the heater power supply. The particulate matter detection device according to this embodiment can repeatedly and accurately detect the particulate matter by oxidizing and removing the particulate matter collected by the collection electrode 51 (i.e., cleaning the collection electrode 51).

The material for the heater 57 is preferably platinum, tungsten, molybdenum, tungsten carbide, or the like. Among these, it is preferable to use platinum that exhibits an accurate resistance-temperature relationship. Since the temperature of the heater 57 can be accurately calculated from the resistance by utilizing platinum as the material for the heater 57, the temperature of the heater 57 can be controlled with high accuracy. The shape and the size of the heater 57 are not particularly limited insofar as the particulate matter collected by the collection electrode 51 can be burned. As the heater power supply (not shown), it is preferable to use a step-down chopper power supply. This makes it possible to efficiently control the temperature of the heater 57. In this case, the switching frequency is preferably 20 kHz or more, and more preferably 20 to 100 kHz. A current applied to the heater 57 from the heater power supply is preferably 0.8 to 4 A. The amount of power consumed by the heater power supply is preferably 30 W or less.

The temperature when oxidizing and removing the particulate matter using the heater 57 is preferably 500 to 900° C., and more preferably 550 to 700° C. If the temperature is less than 500° C., the particulate matter may not be oxidized and removed. If the temperature is more than 900° C., the life of the element may decrease. The period of time in which the particulate matter is oxidized and removed using the heater 57 is preferably 1 to 120 seconds, and more preferably 3 to 30 seconds. If the period of time is less than 1 second, the particulate matter may not be sufficiently oxidized and removed. If the period of time is more than 120 seconds, unnecessary energy consumption may occur. It is preferable to appropriately heat the heater 57 during voltage detection or a corona discharge so as to prevent effects of water (e.g., condensation) when detecting the voltage between the collection electrode and the measurement electrode so that water does not adhere to the collection electrode, for example. In this case, the heating temperature is preferably 200 to 300° C.

As shown in FIGS. 8 and 9, the particulate matter detection device 200 according to this embodiment preferably includes a sheet-shaped heat insulator 58 that is disposed to cover the heater 57. This suppresses radiation of heat generated by the heater 57 so that heat generated by the heater 57 can be efficiently utilized to burn the particulate matter. The material for the heat insulator 58 is not particularly limited, but is preferably a ceramic. It is more preferable that the material for the heat insulator 8 contain at least one component selected from the group consisting of alumina, magnesium oxide, silicon oxide, silicon nitride, aluminum nitride, zirconia, cordierite, mullite, spinel, a magnesium-calcium-titanium oxide, a barium-titanium-zinc oxide, and a barium-titanium oxide. As the ceramic, a porous ceramic, a ceramic fiber, or the like is preferably used. The thickness of the heat insulator is not particularly limited insofar as radiation of heat can be suppressed. The thickness of the heat insulator is preferably about 100 to 1000 µm, for example.

A particulate matter detection device according to another embodiment of the present invention may not include the heater 57, the heater power supply (not shown), and the heat insulator 58 that are included in the particulate matter detection device according to one embodiment of the present invention shown in FIGS. 8 and 9, but may include a power supply (creeping discharge power supply (not shown)) that applies a voltage between the collection electrode 51 and the measurement electrode 55 so that a creeping discharge occurs on the surface of the inter-electrode dielectric 54. The particulate matter collected by the collection electrode can be oxidized and removed by providing the creeping discharge power supply and causing a creeping discharge to occur on the surface of the inter-electrode dielectric. It is preferable to use an alternating-current power supply, a pulse power supply, or the like as the creeping discharge power supply. A voltage applied when causing a creeping discharge is preferably 2 to 15 kV although the voltage differs depending on the thickness of the dielectric and the electrode structure. The amount of power required for causing a creeping discharge is preferably 10 to 30 W. The period of time in which the particulate matter is oxidized and removed by causing a creeping discharge is preferably 1 to 300 seconds, and more preferably 1 to 120 seconds. If the period of time is less than 1 second, the particulate matter may not be sufficiently oxidized and removed. If the period of time is more than 300 seconds, unnecessary energy consumption may occur. The particulate matter detection device according to this embodiment is preferably configured in the same manner as the particulate matter detection device according to one embodiment of the present invention shown in FIGS. 8 and 9, except that the particulate matter detection device according to this embodiment does not include the heater 57, the heater power supply (not shown), and the heat insulator 58, but includes the creeping discharge power supply.

It is preferable that the particulate matter detection device according to one embodiment of the present invention further include a support member, and a laminate that includes the collection electrode, the inter-electrode dielectric, the measurement electrode, the back-side dielectric, the heater, and the heat insulator, and the discharge electrode are secured on the support member, in the same manner as the particulate matter detection device according to the embodiment of the present invention shown in FIG. 6. A structure in which the laminate and the discharge electrode are secured on the support member is preferably the same as that of the particulate matter detection device according to one embodiment of the first invention.

(5) Method of Producing Particulate Matter Detection Device

A method of producing the particulate matter detection device according to one embodiment of the present invention is described below.

(5-1) Preparation of Dielectric-Forming Raw Material

A ceramic raw material that contains at least one component selected from the group consisting of alumina, magnesium oxide, silicon oxide, silicon nitride, aluminum nitride, zirconia, a cordierite-forming raw material, mullite, spinel, a magnesium-calcium-titanium oxide, a barium-titanium-zinc oxide, and a barium-titanium oxide is mixed with other components to prepare a forming raw material (dielectric-forming raw material) in the form of a slurry. Note that the ceramic raw material is preferably but not limited to the above-mentioned components. As the components other than the ceramic raw material, it is preferable to use a binder, a plasticizer, a dispersant, and a solvent (e.g., water or organic solvent). The inter-electrode dielectric and the back-side dielectric are formed using the dielectric-forming raw material. The inter-electrode dielectric and the back-side dielectric may be formed using an identical dielectric-forming raw material, or may be formed using different dielectric-forming raw materials. As the raw material for the inter-electrode dielectric, it is preferable that the ceramic raw material contain alumina or aluminum nitride.

The binder is not particularly limited. An aqueous binder or a non-aqueous binder may be used. As the aqueous binder, methyl cellulose, polyvinyl alcohol, polyethylene oxide, or the like may be suitably used. As the non-aqueous binder, polyvinyl butyral, an acrylic resin, polyethylene, polypropylene, or the like may be suitably used. Examples of the acrylic resin include a (meth)acrylic resin, a (meth)acrylate copolymer, an acrylate-methacrylate copolymer, and the like.

The binder is preferably added in an amount of 3 to 20 parts by mass, and more preferably 6 to 17 parts by mass, based on 100 parts by mass of the ceramic raw material. If the amount of the binder is within the above range, cracks or the like can be prevented when forming the forming raw material in the form of a slurry to produce a green sheet, or when drying and firing the green sheet.

As the plasticizer, glycerol, polyethylene glycol, dibutyl phthalate, di(2-ethylhexyl)phthalate, diisononyl phthalate, or the like may be used.

The plasticizer is preferably added in an amount of 30 to 70 parts by mass, and more preferably 45 to 55 parts by mass, based on 100 parts by mass of the binder. If the amount of the plasticizer is more than 70 parts by mass, the resulting green sheet becomes too soft and may be deformed when processing the green sheet. If the amount of the plasticizer is less than 30 parts by mass, the resulting green sheet becomes too hard so that the handling capability may deteriorate (e.g., cracks may occur when merely bending the green sheet).

As the dispersant, an aqueous dispersant (e.g., anionic surfactant, wax emulsion, or pyridine) or a non-aqueous dispersant (e.g., fatty acid, phosphate, or synthetic surfactant) may be used.

The dispersant is preferably added in an amount of 0.5 to 3 parts by mass, and more preferably 1 to 2 parts by mass, based on 100 parts by mass of the ceramic raw material. If the amount of the dispersant is less than 0.5 parts by mass, the dispersibility of the ceramic raw material may decrease. As a result, the green sheet may produce cracks or the like. If the amount of the dispersant is more than 3 parts by mass, the amount of impurities may increase during firing although the dispersibility of the ceramic raw material remains the same.

Examples of the organic solvent include xylene, butanol, and the like. The organic solvents may be used either individually or in combination. The solvent is preferably added in an amount of 50 to 200 parts by mass, and more preferably 75 to 150 parts by mass, based on 100 parts by mass of the ceramic raw material.

The above-mentioned materials are sufficiently mixed using an alumina pot and alumina cobblestone to prepare a forming raw material slurry for forming a green sheet. The forming raw material slurry may be prepared by mixing the materials by ball milling using a mono ball.

The resulting forming raw material slurry is stirred under reduced pressure to remove bubbles, and the viscosity of the forming raw material slurry is adjusted to a predetermined value. The viscosity of the forming raw material slurry thus prepared is preferably 2.0 to 6.0 Pa·s, more preferably 3.0 to 5.0 Pa·s, and particularly preferably 3.5 to 4.5 Pa·s. The slurry can be easily formed into a sheet by adjusting the viscosity of the slurry within the above range. It may be difficult to form the slurry into a sheet if the viscosity of the slurry is too high or too low. The viscosity of the slurry refers to a value measured using a B type viscometer.

(5-2) Forming

The forming raw material slurry obtained by the above method is formed into a sheet to obtain a green sheet for forming the inter-electrode dielectric and a green sheet for forming the back-side dielectric, if necessary. The forming method is not particularly limited insofar as a green sheet can be formed by forming the forming raw material into a sheet. A doctor blade method, a press forming method, a rolling method, a calender roll method, or the like which is known in the art may be used.

The thickness of the green sheet is preferably 50 to 800 μm.

The electrode (collection electrode and measurement electrode), line, and heater (if necessary) are disposed on the surface of the resulting green sheet. For example, when producing the particulate matter detection device shown in FIG. 8, it is preferable to print the electrodes, lines (not shown), and heater at a corresponding position of the green sheet so that the electrodes, lines, and heater are disposed at predetermined positions. In this case, a conductive paste for forming the electrodes, lines, and heater is prepared. The conductive paste may be prepared by adding a binder and a solvent (e.g., terpineol) to a powder that contains at least one component selected from the group consisting of gold, silver, platinum, nickel, molybdenum, and tungsten, and sufficiently kneading the mixture using a triple roll mill or the like. It is preferable to use platinum for the conductive paste for forming the heater. The conductive paste thus prepared is printed on the surface of the green sheet by screen printing or the like to form the electrodes and the lines having a predetermined shape. The measurement electrode 55 may be printed on the green sheet for forming the inter-electrode dielectric 54, or may be printed on the green sheet for forming the back-side dielectric 56.

The green sheets are then stacked. The green sheets are stacked so that the electrode and heater are disposed as shown in FIG. 8. The green sheets are preferably stacked while applying a pressure.

It is preferable to form the heat insulator by further stacking the green sheet. When forming a porous heat insulator, it is preferable to add a foaming agent to the green sheet slurry, form the slurry into a sheet, and stack the resulting sheet. In this case, since the heat insulator 58 and the dielectric 56 are easily separated during firing, it is important to carefully set the thickness of the heat insulator, the amount of the foaming agent, and the stacking pressure.

(5-3) Firing

The resulting green sheet laminate is dried at 60 to 150° C., and fired at 1200 to 1600° C. to obtain a laminate that includes a collection electrode, an inter-electrode dielectric, a measurement electrode, a back-side dielectric, and a heater that form a particulate matter detection device. When the green sheet contains an organic binder, it is preferable to degrease the green sheet at 400 to 800° C. before firing.

(5-4) Discharge Electrode

It is preferable to use a wire-shaped electrode that contains an Ni alloy as a matrix as the discharge electrode. The wire is preferably obtained by forming a wire rod by wire drawing, and slicing the wire rod by electrical discharge machining or cutting the wire rod using a blade. It is preferable to weld a noble metal containing Pt that exhibits durability as the main component to the end (discharge section) of the discharge electrode.

(5-5) Support Member

The support member is preferably formed of a ceramic sintered body (e.g., alumina or aluminum nitride). It is preferable to form a hole in the support member in the axial direction toward the discharge electrode. The wire that forms the discharge electrode is inserted into the hole. It is preferable to form folds or the like on the support member by cutting work or the like. For example, the support member is preferably formed to have a shape similar to that of the support member 43 shown in FIG. 6.

(5-6) Discharge Power Supply

The discharge power supply is preferably a power supply that includes a one-transistor flyback step-up power supply having a simple circuit configuration and a rectifier circuit.

(5-7) Measurement Section

It is preferable to use a voltmeter having an excellent response capability as the measurement section. The resistor 64 (see FIG. 8) connected in parallel with the measurement section is not particularly limited. A known resistor having a given resistance may be used.

(5-8) Heater Power Supply

As the heater power supply, it is preferable to use a step-down chopper switching power supply using a self-arc-extinguishing semiconductor switch. It is more preferable to use a power supply that calculates the temperature of the heater from the heater voltage and current and has a temperature control function.

(5-9) Production of Particulate Matter Detection Device

It is preferable to secure the laminate and the discharge electrode on the support member so that the end of the discharge electrode faces the collection electrode of the laminate. For example, it is preferable to form the support member 43 shown in FIG. 6, mount the discharge electrode 52 on the end 41, and mount the laminate 44 on the support stage 42. It is preferable to connect the discharge power supply 59 to the collection electrode 51 and the discharge electrode 52 through the resistor 63 shown in FIG. 8. It is preferable to connect the measurement section to the collection electrode and the measurement electrode, connect the resistor 64 (see FIG. 8) in parallel with the measurement section, and optionally connect the heater power supply to the heater. The particulate matter detection device according to this embodiment can be produced in this manner.

(Fourth Invention)

(6) Particulate Matter Detection Method

A particulate matter detection method according to one embodiment of the present invention (fourth invention) is described below.

The particulate matter detection method according to this embodiment includes charging particulate matter contained in gas by utilizing a corona discharge, and detecting the voltage between a collection electrode and a measurement electrode while collecting the charged particulate matter by the collection electrode by utilizing an electrostatic force to detect the particulate matter contained in the gas. Since the particulate matter detection method according to this embodiment detects the particulate matter by detecting the voltage between the collection electrode and the measurement electrode that changes due to the collected particulate matter, the particulate matter can be simply detected while reducing a measurement error in the same manner as the particulate matter detection device according to the present invention. Moreover, the particulate matter can be detected while collecting the particulate matter.

The particulate matter detection method according to this embodiment is preferably carried out using the particulate matter detection device according to the present invention. It is preferable to install the particulate matter detection device according to the present invention in an exhaust pipe of a diesel engine or the like, charge and collect the particulate matter, and detect a change in voltage to detect the particulate matter contained in the gas (exhaust gas) inside the exhaust pipe. It is preferable that a specific embodiment and usage of each element of the particulate matter detection device used for the particulate matter detection method according to this embodiment be the same as a specific embodiment and usage of each element of the particulate matter detection device according to the present invention.

In the particulate matter detection method according to this embodiment, the operation of charging and collecting the particulate matter includes charging the particulate matter contained in the gas by utilizing a corona discharge, and collecting the charged particulate matter by the collection electrode by utilizing an electrostatic force. The method of charging the particulate matter by utilizing a corona discharge is not particularly limited. It is preferable to charge the particulate matter contained in the gas by utilizing a corona discharge that occurs when applying a high voltage between the discharge electrode and the collection electrode of the particulate matter detection device according to the present invention. The method of collecting the charged particulate matter by the collection electrode by utilizing an electrostatic force is not particularly limited. Since a high voltage is applied between the discharge electrode and the collection electrode when using the particulate matter detection device according to the present invention, the charged particulate matter is collected by the collection electrode (positive electrode) having a different polarity due to the electrostatic force.

In the particulate matter detection method according to this embodiment, the operation of detecting the voltage between the collection electrode and the measurement electrode is carried out in parallel with the operation of charging and collecting the particulate matter. The method of detecting the voltage between the collection electrode and the measurement electrode is not particularly limited. It is preferable to detect the voltage between the collection electrode and the measurement electrode using the measurement section of the particulate matter detection device according to the present invention. It is preferable to detect the particulate matter by calculating the amount of particulate matter from the difference between the voltage between the collection electrode and the measurement electrode when the particulate matter is absent and the voltage between the collection electrode and the measurement electrode when the particulate matter has been collected by the collection electrode.

In the particulate matter detection method according to this embodiment, it is preferable to detect the particulate matter using the particulate matter detection device according to the present invention that includes the heater for oxidizing and removing the collected particulate matter. This aims at detecting the particulate matter after oxidizing and removing the particulate matter collected by the collection electrode using the heater. The particulate matter detection device according to the present invention that is configured so that the particulate matter is oxidized and removed by causing a creeping discharge using the collection electrode may also be used. The particulate matter can be steadily detected for a long period of time by repeating a cycle that includes oxidizing and removing the particulate matter collected by the collection electrode, detecting the particulate matter, and then oxidizing and removing the particulate matter.

The particulate matter detection method according to this embodiment charges the particulate matter by utilizing a corona discharge, and detects the voltage between the collection electrode and the measurement electrode while collecting the charged particulate matter by the collection electrode. It is preferable to oxidize and remove the collected particulate matter using a heater or by a creeping discharge using the collection electrode after detecting the voltage between the collection electrode and the measurement electrode. It is preferable to then charge the particulate matter by utilizing a corona discharge and detect the voltage between the collection electrode and the measurement electrode while collecting the charged particulate matter by the collection electrode.

As shown in FIG. 7, when the particulate matter detection device according to the third invention is installed in an exhaust pipe 37 of an automotive diesel engine 31, for example, it is preferable to cause a corona discharge when the engine speed, torque, and the like of the diesel engine 31 and the flow rate, the temperature, and the like of an exhaust gas 38 have satisfied given conditions. Each element shown in FIG. 7 is preferably similar to each element used in the particulate matter detection method according to the second invention.

The period of time in which the particulate matter is charged by utilizing a corona discharge and collected by the collection electrode while detecting the voltage is preferably 0.001 to 300 seconds, and more preferably 0.1 to 60 seconds. If the period of time is less than 0.001 second, the measurement accuracy of the amount of particulate matter may decrease due to a decrease in the amount of particulate matter collected. If the period of time is more than 300 seconds, since the amount of particulate matter collected increases, it may be difficult to accurately determine the amount of particulate matter collected by detecting the voltage.

The period of time in which the particulate matter is oxidized and removed using the heater is preferably 1 to 300 seconds, and more preferably 1 to 120 seconds. If the period of time is less than 1 second, the particulate matter may not be sufficiently oxidized and removed. If the period of time is more than 300 seconds, unnecessary energy consumption may occur. The period of time in which the particulate matter is oxidized and removed by causing a creeping discharge is preferably 1 to 120 seconds, and more preferably 3 to 30 seconds. If the period of time is less than 1 second, the particulate matter may not be sufficiently oxidized and removed. If the period of time is more than 120 seconds, unnecessary energy consumption may occur.

Examples

The present invention is further described below by way of examples. Note that the present invention is not limited to the following examples.

Example 1

Laminate of Electrodes, Dielectrics, Etc.

An alumina pot was charged with alumina (ceramic raw material), polyvinyl butyral (binder), di(2-ethylhexyl)phthalate (plasticizer), sorbitan trioleate (dispersant), and an organic solvent (xylene:butanol=6:4 (mass ratio)). The components were mixed to prepare a forming raw material slurry for forming a green sheet. 7 parts by mass of the binder, 3.5 parts by mass of the plasticizer, 1.5 parts by mass of the dispersant, and 100 parts by mass of the organic solvent were used based on 100 parts by mass of alumina.

The resulting forming raw material slurry for green sheet was stirred under reduced pressure to remove bubbles, and the viscosity of the forming raw material slurry was adjusted to 4 Pa·s. The viscosity of the slurry was measured using a B type viscometer.

The forming raw material slurry obtained by the above method was formed into a sheet using a doctor blade method. The thickness of the green sheet was 250 μm. The green sheets for the inter-electrode dielectric and the back-side dielectric were formed of the same material.

Electrodes and lines were formed on the surface of the resulting green sheet. A conductive paste for forming an electrodes and lines was prepared by adding polyvinyl butyral (binder), di(2-ethylhexyl)phthalate (plasticizer), sorbitan trioleate (dispersant), 2-ethylhexanol (solvent), alumina (green sheet common material), and a glass frit (sintering aid) to a platinum powder, and sufficiently kneading the mixture using a triple roll mill (platinum:alumina:glass frit:2-ethylhexanol: polyvinyl butyral:di(2-ethylhexyl)phthalate:sorbitan trioleate=80:15:5:50:7:3.5:1 (mass ratio)). The conductive paste thus prepared was screen-printed on the surface of the green sheet to form electrodes and lines having a predetermined shape. The collection electrode was provided with elevations and depressions (see FIG. 2B). The above-mentioned green sheet was used for the inter-electrode dielectric 4 and the back-side dielectric 6. The above-mentioned green sheet was also used for the heat insulator 8. The collection electrode 1, the measurement electrode 5, and the heater 7 were formed by printing the above-mentioned conductive paste to a thickness of 50 μm.

The green sheets were stacked under pressure using a heating-type uniaxial press machine to obtain an unfired laminate of the collection electrode 1, the inter-electrode dielectric 4, the measurement electrode 5, the back-side dielectric 6, the heater 7, and the heat insulator 8 shown in FIG. 1.

The green sheet laminate thus obtained was dried at 120° C., and fired at 1500° C. to obtain a laminate of the electrodes, the dielectrics, etc.

(Support Member)

A support member having a structure shown in FIG. 6 was formed. The support member was formed of a ceramic sintered body made of alumina. A hole having a diameter of 2 mm was formed in the support member in the axial direction toward the discharge electrode. Folds and the like were formed on the support member by cutting work.

(Measurement Section)

"4194A" manufactured by Agilent Technologies was used as the measurement section.

(Discharge Electrode)

The discharge electrode was formed by wire-drawing a wire rod containing an Ni alloy matrix to have a diameter of 2 mm, and slicing the wire rod by electrical discharge machining. The discharge electrode was pressed into the support member, and secured using a ceramic heat-resistant adhesive. A noble metal containing Pt exhibiting durability as the main component was welded to the end (discharge section) of the discharge electrode, and formed in the shape of a needle by electrical discharge machining.

(Discharge Power Supply)

A high-voltage DC power supply was used as the discharge power supply.

(Heater Power Supply)

A DC power supply having a temperature control function was used as the heater power supply.

(Particulate Matter Detection Device)

The laminate of the electrodes, the dielectrics, etc. and the discharge electrode were secured on the support member, and the discharge power supply, the heater power supply, and the measurement section were connected to the electrodes to obtain a particulate matter detection device.

(Particulate Matter Measurement 1)

The particulate matter detection device was installed in an exhaust pipe of a diesel engine. A direct injection diesel engine (displacement: 2000 cc) was used as the diesel engine. An exhaust gas was discharged at an engine speed of 2000 rpm, a torque of 36 N·m, an exhaust gas recirculation (EGR) rate of 0%, an exhaust gas temperature of 295° C., and an air intake of 2 m³/min (room temperature). The amount of particulate matter contained in the exhaust gas measured using a smoke meter (manufactured by AVL, model: 4158) was 1.69 mg/m³. The particulate matter was detected in five cycles (one cycle consisting of "particulate matter charging-collection" (5 seconds) and "impedance change detection" (10 seconds)) while discharging the exhaust gas from the diesel engine. The particulate matter was not burned using the heater. A change in impedance was detected by measuring the capacitance (pF) between the collection electrode and the measurement electrode. When detecting the particulate matter, the voltage applied by the discharge power supply was set at DC 5.2 kV, the voltage applied by the measurement section was set at AC 2 V, and the frequency was set at 1 kHz. The measurement results (measurement 1 (pF)) obtained in the first cycle and the fifth cycle are shown in Table 1.

(Particulate Matter Measurement 2)

The particulate matter detection device was installed in an exhaust pipe of a diesel engine. A direct injection diesel engine (displacement: 2000 cc) was used as the diesel engine. An exhaust gas was discharged at an engine speed of 2400 rpm, a torque of 69 N·m, an exhaust gas recirculation (EGR)

of 50%, an exhaust gas temperature of 300° C., and an air intake of 2 m$^3$/min (room temperature). The amount of particulate matter contained in the exhaust gas measured using a smoke meter (manufactured by AVL, model: 4158) was 7.83 mg/m$^3$. The particulate matter was detected in five cycles (one cycle consisting of "particulate matter charging-collection" (5 seconds) and "impedance change detection" (10 seconds) while discharging the exhaust gas from the diesel engine. The particulate matter was not burned using the heater. A change in impedance was detected by measuring the capacitance pF) between the collection electrode and the measurement electrode. When detecting the particulate matter, the voltage applied by the discharge power supply was set at DC 5.2 kV, the voltage applied by the measurement section was set at AC 2 V, and the frequency was set at 1 kHz. The measurement results (measurement 2 (pF)) obtained in the first cycle and the fifth cycle are shown in Table 1.

TABLE 1

|  |  | Example 1 |
|---|---|---|
| Measurement 1 (pF) | First cycle | 0 |
|  | Fifth cycle | 2 |
| Measurement 2 (pF) | First cycle | 5 |
|  | Fifth cycle | 15 |

Table 1 clearly shows the difference in capacitance (impedance) between the measurement 1 and the measurement 2 even in the first cycle. Specifically, an increase in the amount of particulate matter contained in the exhaust gas could be detected even when measuring the impedance for 5 seconds. The difference in capacitance (impedance) between the measurement 1 and the measurement 2 became significant when the capacitance was measured in five cycles, so that an increase in the amount of particulate matter contained in the exhaust gas could be detected more accurately.

Example 2

A particulate matter detection device similar to the particulate matter detection device 200 shown in FIG. 8 was produced, except that the back-side electrode 56, the heater 57, and the heat insulator 58 were not provided.

(Laminate of Electrodes, Inter-Electrode Dielectric, etc.)

An alumina pot was charged with alumina (ceramic raw material), polyvinyl butyral (binder), di(2-ethylhexyl)phthalate (plasticizer), sorbitan trioleate (dispersant), and an organic solvent (xylene:butanol=6:4 (mass ratio)). The components were mixed to prepare a forming raw material slurry for forming a green sheet. 7 parts by mass of the binder, 3.5 parts by mass of the plasticizer, 1.5 parts by mass of the dispersant, and 100 parts by mass of the organic solvent were used based on 100 parts by mass of alumina.

The resulting forming raw material slurry was stirred under reduced pressure to remove bubbles, and the viscosity of the forming raw material slurry was adjusted to 4 Pa·s. The viscosity of the slurry was measured using a B type viscometer.

The forming raw material slurry obtained by the above method was formed into a sheet using a doctor blade method to obtain a green sheet for forming an inter-electrode dielectric. The thickness of the green sheet was 500 μm.

Electrodes and lines were formed on the surface of the resulting green sheet. A conductive paste for forming the electrodes and the lines was prepared by adding polyvinyl butyral (binder), di(2-ethylhexyl)phthalate (plasticizer), sorbitan trioleate (dispersant), 2-ethylhexanol (solvent), alumina (green sheet common material), and a glass frit (sintering aid) to a platinum powder, and sufficiently kneading the mixture using a triple roll mill (platinum:alumina:glass frit:2-ethylhexanol:polyvinyl butyral:di(2-ethylhexyl)phthalate:sorbitan trioleate=80:15:5:50:7:3.5:1 (mass ratio)). The conductive paste thus prepared was screen-printed on the surface of the green sheet to form electrodes and lines having a predetermined shape. The collection electrode (20×20 mm) was provided with elevations and depressions (see FIG. 10B). The number of elevations of the collection electrode was three. The width of the elevation (electrode) was 1 mm, and the pitch between the elevations was 8.5 mm. The dimensions of the measurement electrode 55 were 20×20 mm. The thickness of the inter-electrode dielectric 54 was 0.5 mm. The collection electrode 51 and the measurement electrode 55 were formed by printing the above-mentioned conductive paste to a thickness of 50 μm.

The green sheets were stacked under pressure using a heating-type uniaxial press machine to obtain an unfired laminate of the collection electrode 51, the inter-electrode dielectric 54, and the measurement electrode 55 shown in FIG. 8.

The laminate of the green sheets and the electrodes thus obtained were dried at 120° C., and fired at 1500° C.

(Support Member)

A support member having a structure shown in FIG. 6 was formed. The support member was formed of a ceramic sintered body made of alumina. A hole having a diameter of 2 mm was formed in the support member in the axial direction toward the discharge electrode. Folds and the like were formed on the support member by cutting work.

(Measurement Section)

A digital multimeter (voltmeter) (manufactured by Sanwa Electric Instrument Co., Ltd.) was used as the measurement section. A metal film resistor (2.2 MΩ) was used as the resistor connected to the measurement section.

(Discharge Electrode)

The discharge electrode was formed by forming a wire rod containing an Ni alloy to have a diameter of 2 mm by wire drawing, and slicing the wire rod by electrical discharge machining. The discharge electrode was pressed into the support member, and secured using a ceramic heat-resistant adhesive. A noble metal containing Pt exhibiting durability as the main component was welded to the end (discharge section) of the discharge electrode, and formed in the shape of a needle by electrical discharge machining.

(Discharge Power Supply)

A high-voltage DC power supply was used as the discharge power supply.

(Particulate Matter Detection Device)

The laminate of the electrodes, the dielectric, etc. and the discharge electrode were secured on the support member, and the discharge power supply and the measurement section (and the resistor) were connected to the electrodes to obtain a particulate matter detection device.

(Particulate Matter Measurement)

The particulate matter detection device was installed in an exhaust pipe of a diesel engine. A direct injection diesel engine (displacement: 2000 cc) was used as the diesel engine. An exhaust gas was discharged at an engine speed of 2000 rpm, a torque of 36 N·m, an exhaust gas recirculation (EGR) rate of 0%, an exhaust gas temperature of 295° C., and an air intake of 2 m$^3$/min (room temperature). The particulate matter was collected from the exhaust gas and used for experiments.

A corona discharge was caused to occur at a voltage of 7 kV and a discharge current of 0.01 mA, and the voltage between the collection electrode and the measurement electrode was measured. An insulating spoon on which particulate matter was placed was moved close to the corona discharge electrode so that the particulate matter was collected by the collection electrode, and the voltage between the collection electrode and the measurement electrode was again measured.

The voltage measured by the measurement section in a state in which the particulate matter was absent was 8.45 V. When the insulating spoon on which the particulate matter was placed was moved close to the corona discharge electrode so that the particulate matter was collected by the collection electrode, the voltage measured by the measurement section was 8.28 V.

The change in the voltage between the collection electrode and the measurement electrode was −0.17 V, and the corresponding amount of particulate matter collected was 270 μg. The amount of particulate matter collected was obtained by measuring the amount of particulate matter deposited on the laminate of the electrodes and the dielectric. Specifically, the amount of particulate matter collected can be determined (detected) by detecting the voltage between the collection electrode and the measurement electrode.

INDUSTRIAL APPLICABILITY

The amount of particulate matter discharged can be reduced by detecting the amount of particulate matter contained in a flue gas or a diesel engine exhaust gas. This makes it possible to prevent air pollution.

The invention claimed is:

1. A particulate matter detection device that is disposed in a gas passage that allows gas containing particulate matter to pass through and detects the particulate matter contained in the gas, the particulate matter detection device comprising a collection electrode that collects the particulate matter, a discharge electrode that allows a corona discharge to occur when a voltage is applied between the collection electrode and the discharge electrode, a measurement electrode, the impedance between the collection electrode and the measurement electrode changing when the collection electrode has collected the particulate matter, and a measurement section that detects a change in the impedance between the collection electrode and the measurement electrode, the particulate matter detection device detecting the particulate matter by charging the particulate matter contained in the gas by utilizing the corona discharge, collecting the charged particulate matter by the collection electrode by utilizing an electrostatic force, and detecting a change in the impedance between the collection electrode that has collected the particulate matter and the measurement electrode using the measurement section.

2. The particulate matter detection device according to claim 1, further comprising an inter-electrode dielectric that is disposed on the side of the collection electrode opposite to the side that faces the discharge electrode, wherein the measurement electrode is disposed on the side of the inter-electrode dielectric opposite to the side on which the collection electrode is disposed.

3. The particulate matter detection device according to claim 2, further comprising a back-side dielectric that is disposed on the side of the measurement electrode opposite to the side on which the inter-electrode dielectric is disposed, and wherein a heater is disposed on the surface of the back-side dielectric opposite to the side on which the measurement electrode is disposed, wherein the particulate matter collected by the collection electrode is oxidized and removed by heat generated by the heater.

4. The particulate matter detection device according to claim 2, further comprising a power supply that applies a voltage between the collection electrode and the measurement electrode so that a creeping discharge occurs on the surface of the inter-electrode dielectric, wherein the particulate matter collected by the collection electrode is oxidized and removed by the creeping discharge.

5. The particulate matter detection device according to claim 1, further comprising a dielectric that is disposed on the side of the collection electrode opposite to the side that faces the discharge electrode, wherein the measurement electrode is disposed on the side of the dielectric on which the collection electrode is disposed.

6. The particulate matter detection device according to claim 5, further comprising a heater that is disposed on the surface of the dielectric, wherein the particulate matter collected by the collection electrode is oxidized and removed by heat generated by the heater.

* * * * *